(12) United States Patent
Tokuhisa

(10) Patent No.: US 10,559,937 B2
(45) Date of Patent: Feb. 11, 2020

(54) PULSED LIGHT GENERATION DEVICE, PULSED LIGHT GENERATION METHOD, EXPOSURE APPARATUS HAVING PULSED LIGHT GENERATION DEVICE AND INSPECTION APPARATUS HAVING PULSED LIGHT GENERATION DEVICE

(71) Applicant: NIKON CORPORATION, Tokyo (JP)

(72) Inventor: Akira Tokuhisa, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 16/200,106

(22) Filed: Nov. 26, 2018

(65) Prior Publication Data

US 2019/0131756 A1 May 2, 2019

Related U.S. Application Data

(63) Continuation of application No. PCT/JP2017/018852, filed on May 19, 2017.

(30) Foreign Application Priority Data

May 26, 2016 (JP) ................................. 2016-105612

(51) Int. Cl.
*H01S 3/10* (2006.01)
*G01N 21/956* (2006.01)
(Continued)

(52) U.S. Cl.
CPC ....... *H01S 3/10023* (2013.01); *G01N 21/956* (2013.01); *G02F 1/3532* (2013.01);
(Continued)

(58) Field of Classification Search
CPC ............... H01S 3/10023; H01S 3/0677; H01S 3/094076; G01N 21/956;
(Continued)

(56) References Cited

U.S. PATENT DOCUMENTS

| 6,718,142 B1 * | 4/2004 | Murai | H04B 10/25077 398/155 |
| 2006/0018586 A1 * | 1/2006 | Kishida | G01B 11/16 385/12 |
| 2013/0230071 A1 | 9/2013 | Haensel et al. | |

FOREIGN PATENT DOCUMENTS

| JP | 7-58698 | 3/1995 |
| JP | 7-58699 | 3/1995 |

(Continued)

OTHER PUBLICATIONS

International Search Report dated Aug. 8, 2017 in corresponding International Application No. PCT/JP2017/018852.

*Primary Examiner* — Jerry M Blevins

(57) ABSTRACT

A pulsed light generation device, includes: a first optical fiber through which first pulsed light and second pulsed light, having an intensity that decreases while an intensity of the first pulsed light increases, and increases while the intensity of the first pulsed light decreases, having been multiplexed and entered therein, are propagated; and a second optical fiber at which the first pulsed light, having exited the first optical fiber and entered therein, is amplified while being propagated therein, wherein: at the first optical fiber, phase modulation occurs in the first pulsed light due to cross phase modulation caused by the second pulsed light; and self-phase modulation occurring in the first pulsed light at the second optical fiber is diminished by the phase modulation having occurred at the first optical fiber.

28 Claims, 20 Drawing Sheets

(51) Int. Cl.
    *G02F 1/35*         (2006.01)
    *G03F 7/20*         (2006.01)
    *H01S 3/067*       (2006.01)
    *H01S 3/094*       (2006.01)
    *G02F 1/355*       (2006.01)

(52) U.S. Cl.
    CPC ........ *G03F 7/70041* (2013.01); *H01S 3/0677* (2013.01); *H01S 3/094076* (2013.01); *G01N 2021/95676* (2013.01); *G02F 1/3551* (2013.01); *G02F 2001/354* (2013.01)

(58) Field of Classification Search
    CPC ........ G01N 2021/95676; G02F 1/3532; G02F 1/3551; G02F 2001/354; G03F 7/70041
    USPC .......................................................... 385/1
    See application file for complete search history.

(56) References Cited

FOREIGN PATENT DOCUMENTS

| | | |
|---|---|---|
| JP | 8-116307 | 5/1996 |
| JP | 8-125605 | 5/1996 |
| JP | 9-236781 | 9/1997 |
| JP | 2007-300496 | 11/2007 |
| JP | 2011-49296 | 3/2011 |
| JP | 2012-2965 | 1/2012 |
| JP | 2012-54500 | 3/2012 |
| JP | 5211487 | 3/2013 |
| JP | 2013-187542 | 9/2013 |
| JP | 2014-224917 | 12/2014 |
| JP | 5648969 | 1/2015 |
| WO | WO 02/095486 | 11/2002 |
| WO | WO 2014/141973 A1 | 9/2014 |

\* cited by examiner

PULSED LIGHT GENERATION DEVICE, PULSED LIGHT GENERATION METHOD, EXPOSURE APPARATUS HAVING PULSED LIGHT GENERATION DEVICE AND INSPECTION APPARATUS HAVING PULSED LIGHT GENERATION DEVICE

CROSS REFERENCE TO RELATED APPLICATIONS

This application is a continuation of international application No. PCT/JP2017/018852 filed May 19, 2017, which claims the foreign priority benefit to Japanese Patent Application No. 2016-105612, filed May 26, 2016.

The disclosures of the following priority applications are herein incorporated by reference: International application No. PCT/JP2017/018852 filed May 19, 2017 and Japanese Patent Application No. 2016-105612, filed May 26, 2016.

BACKGROUND ART

1. Technical Field

The present invention relates to a pulsed light generation device, a pulsed light generation method, an exposure apparatus having the pulsed light generation device and an inspection apparatus having the pulsed light generation device.

2. Description of Related Art

When using pulsed light emitted from a laser such as a semiconductor laser as a light source for an inspection apparatus or a processing apparatus, it is required to emit pulsed light with high intensity and narrow wavelength spectral width. In order to obtain pulsed light with high intensity, it is necessary to amplify pulsed light having been emitted from a semiconductor laser by an optical fiber amplifier. However, phase modulation occurs in the pulsed light through self-phase modulation while it is being amplified, resulting in broadening of the pulsed light wavelength spectrum.

Japanese Laid Open Patent Publication No. H8-125605 discloses an optical communication system used for signal light communication, in which signal light achieved by multiplexing signal light that has undergone intensity modulation executed in correspondence to binary signal data, and inverted signal light that has undergone intensity modulation executed in correspondence to an inverted binary signal generated by inverting the binary signal data, is transmitted through an optical fiber transmission path.

SUMMARY

The optical communication system disclosed in Japanese Laid Open Patent Publication No. H8-125605 comes up short in that the pulsed light cannot be amplified to achieve a high level of intensity while suppressing any broadening of the wavelength spectrum.

According to the first aspect of the present invention, a pulsed light generation device comprises: a first optical fiber through which first pulsed light and second pulsed light, having an intensity that decreases while an intensity of the first pulsed light increases, and increases while the intensity of the first pulsed light decreases, having been multiplexed and entered therein, are propagated; and a second optical fiber at which the first pulsed light, having exited the first optical fiber and entered therein, is amplified while being propagated therein, wherein: at the first optical fiber, phase modulation occurs in the first pulsed light due to cross phase modulation caused by the second pulsed light; and self-phase modulation occurring in the first pulsed light at the second optical fiber is diminished by the phase modulation having occurred at the first optical fiber.

According to the second aspect of the present invention, a pulsed light generation method comprises steps of: multiplexing first pulsed light and second pulsed light, having an intensity that decreases while an intensity of the first pulsed light increases, and increases while the intensity of the first pulsed light decreases, and causing the multiplexed first pulsed light and second pulsed light to enter a first optical fiber to be propagated therein; causing the first pulsed light, having exited the first optical fiber, to enter a second optical fiber and amplifying the first pulsed light as the first pulsed light is propagated through the second optical fiber; and diminishing phase modulation occurring in the first pulsed light at the second optical fiber, attributable to self-phase modulation, with phase modulation occurring in the first pulsed light at the first optical fiber, attributable to cross phase modulation caused by the second pulsed light.

DESCRIPTION OF EMBODIMENTS

First Embodiment

Figure 1:
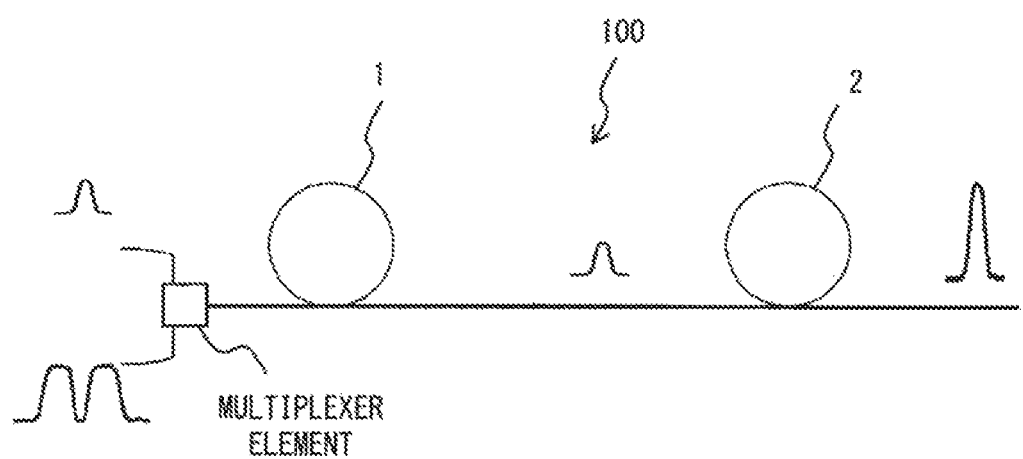
FIG. 1 is a conceptual diagram illustrating the pulsed light generation device according to the first embodiment.

The following is a description of the pulsed light generation device according to the first embodiment of the present invention, given in reference to drawings. FIG. 1 is a conceptual diagram illustrating the pulsed light generation device according to the first embodiment. As shown in FIG. 1, a pulsed light generation device 100 comprises a first optical fiber 1 to which multiplexed light, achieved by multiplexing first pulsed light and second pulsed light whose waveforms are different from each other, enter, and a second optical fiber 2 disposed on a downstream side relative to the first optical fiber 1, from which the first pulsed light, having entered therein after having exited the first optical fiber 1, and having been amplified therein, exits. The first pulsed light is pulsed light that is amplified in the second optical fiber 2 and hereafter will be referred to as main pulsed light. The second pulsed light is pulsed light that induces phase modulation in the main pulsed light through cross phase modulation and hereafter will be referred to as sub pulsed light.

The main pulsed light may be generated by, for instance, modulating, via a modulator (not shown), pulsed light or continuous light emitted from a laser such as a DFB laser (distributed feedback laser: not shown) so as to achieve a desired pulse duration and a desired pulse interval. The sub pulsed light may be generated by, for instance, modulating, via a modulator (not shown), pulsed light or continuous light emitted from a laser such as a DFB laser, so as to achieve a desired waveform, different from that of the main pulsed light. A multiplexer element that multiplexes the main pulsed light and the sub pulsed light may be a multiplexer adopting, for instance, the wavelength division multiplexing method.

Figure 2:
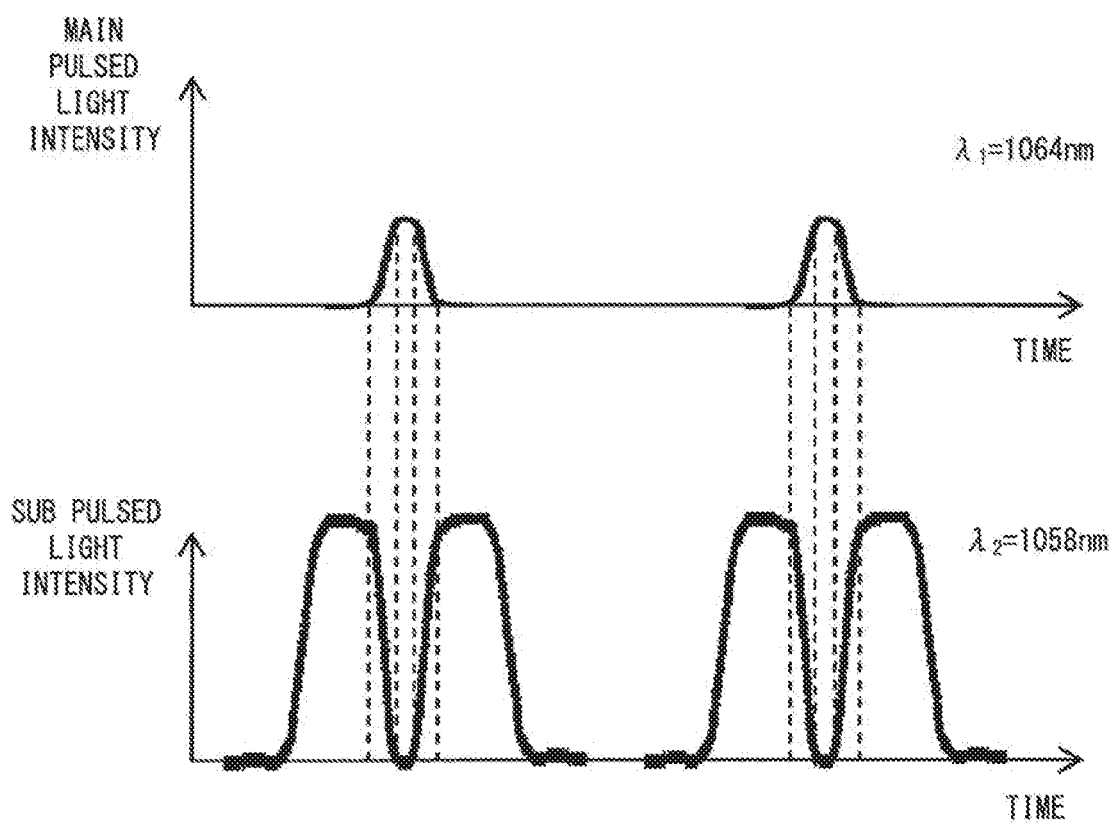
FIG. 2 is a conceptual diagram indicating the relationship between the waveforms of the main pulsed light and the sub pulsed light.

FIG. 2 is a conceptual diagram indicating the relationship between the waveform of the main pulsed light and that of the sub pulsed light. As FIG. 2 indicates, the main pulsed light and the sub pulsed light are emitted in synchronization with each other so as to achieve the following relationship. Namely, while the intensity of the main pulsed light increases (rises), the intensity of the sub pulsed light decreases (falls), and while the intensity of that main pulsed light decreases (falls), the intensity of the sub pulsed light increases (rises). Since a rise of the sub pulsed light is completed at a time point preceding the start of a rise of the main pulsed light, the sub pulsed light is allowed to fall while the main pulsed light rises. In addition, a fall of the sub pulsed light is completed at a time point that occurs after a fall of the main pulsed light is completed.

In other words, the sub pulsed light is made up with a pair of pulses (a preceding pulse and a following pulse) with two peaks, and the waveform between the two pulses has a complementary relation to the waveform of the main pulsed light. In FIG. 2, the intensity of the sub pulsed light at the point between the two pulses in the pair is zero. While it is preferred that the intensity of the sub pulsed light at the point between the two pulses be zero, it is nonessential to achieve precisely zero intensity, as long as the intensity at the point between the two pulses is sufficiently low compared to the intensity levels measured at preceding and following time points.

It is preferred that the peak intensity of the main pulsed light be sufficiently lower than the peak intensity of the sub pulsed light at the time point at which the main pulsed light and the sub pulsed light enter the first optical fiber 1. For instance, it is preferred that the peak intensity of the main pulsed light be equal to or lower than 1/1000 of the peak intensity of the sub pulsed light.

The broadening of the wavelength spectrum occurring as pulsed light is propagated through an optical fiber will be explained next. As pulsed light is propagated through an optical fiber, phase modulation $\phi_{SPM}$ attributable to self-phase modulation (SPM) is induced by a change in intensity of the pulsed light itself. This phase modulation $\phi_{SPM}$ causes a broadening of the wavelength spectrum of the pulsed light. This broadening of the wavelength spectrum is referred to as a chirp. Accordingly, in order to suppress the chirp, it is necessary to reduce the extent of the phase modulation mentioned above.

If through the optical fiber, other pulsed light is also propagated simultaneously with the pulsed light explained above, phase modulation $\phi_{XPM}$ is induced through cross phase modulation (XPM) as the intensity of the other pulsed light changes, in addition to the phase modulation $\phi_{SPM}$ through the SPM explained above. The phase modulation $\phi_{XPM}$ too, causes a broadening of the wavelength spectrum of the pulsed light. Namely, the extent to which the wavelength spectrum broadens as the pulsed light is propagated through the optical fiber is dependent upon the phase modulation $\phi_{SPM}+\phi_{XPM}$.

In the pulsed light generation device 100 shown in FIG. 1, the main pulsed light and the sub pulsed light are multiplexed, and then the multiplexed light enters the first optical fiber 1 and propagates therein. As explained above, in the first optical fiber 1, the main pulsed light is subjected to phase modulation $\phi_{XPM1}$ through the XPM from the sub pulsed light, as well as phase modulation $\phi_{SPM1}$ through SPM. Total phase modulation $\phi_1$, to which the main pulsed light is subjected as it is propagated through the first optical fiber 1 can be expressed as; $\phi_1=\phi_{SPM1}+\phi_{XPM1}$. The main pulsed light and the sub pulsed light are synchronized so that the intensities of the main pulsed light and the sub pulsed light change oppositely to each other with time. Namely, the intensity of the sub pulsed light decreases while the intensity of the main pulsed light increases, and the intensity of the sub pulsed light increases while the intensity of the main pulsed light decreases. This means that the directions of the phase modulation $\phi_{SPM1}$ and the phase modulation $\phi_{XPM1}$ are opposite from each other, i.e., $\phi_{SPM1}$ and $\phi_{XPM1}$ take opposite signs (it is to be noted, however, that the DC component of phase offset, which is not a contributing factor with respect to wavelength spectrum broadening, is not considered in the description).

The main pulsed light, having exited the first optical fiber 1, enters the second optical fiber 2 and is propagated through the second optical fiber 2. At the entrance of the second optical fiber 2, the peak intensity of the sub pulsed light must be zero, i.e., it is necessary to ensure that no sub pulsed light enters the second optical fiber 2, or the peak intensity of the sub pulsed light entering the second optical fiber 2 must be very low level. Such a condition may be achieved by having the sub pulsed light absorbed in the first optical fiber 1 or by separating the sub pulsed light between the first optical fiber 1 and the second optical fiber 2. The second optical fiber 2 is used for amplification of the main pulsed light, and thus, if light within the amplification band other than the main pulsed light enters the second optical fiber 2, the amplification gain at the second optical fiber 2 will be expended in order to amplify the other light, resulting in lowered amplification efficiency for the main pulsed light.

At the second optical fiber 2, phase modulation $\phi_{SPM2}$ occurs in the main pulsed light due to SPM induced as the intensity of the main pulsed light itself changes. As explained above, the intensity of the sub pulsed light entering the second optical fiber 2 is zero or extremely low, and thus, any phase shift occurring in the main pulsed light due to XPM induced as the intensity of the sub pulsed light changes, is insignificant, and can be disregarded. Accordingly, total phase modulation $\phi_2$ in the main pulsed light as it is propagated through the second optical fiber 2 can be expressed as $\phi_2 = \phi_{SPM2}$.

Thus, total phase modulation $\phi_{TOT}$ (=$\phi_1+\phi_2$) occurring in the main pulsed light having been propagated through the first optical fiber 1 and the second optical fiber 2 can be expressed as;

$$\phi_{TOT} = \phi_{SPM1} + \phi_{XPM1} + \phi_{SPM2} \quad (1)$$

$\phi_{SPM1}$ and $\phi_{SPM2}$ in equation (1) bear a sign that is the opposite of the sign taken for $\phi_{XPM1}$. This means that if the absolute value of $\phi_{SPM1} + \phi_{SPM2}$ is equal to the absolute value of $\phi_{XPM1}$, the total phase modulation $\phi_{TOT}$ is zero. In this case, too, the DC component phase offset, which does not contribute to broadening of the main pulsed light wavelength spectrum, is disregarded. The DC component phase offset is likewise disregarded in the following description. Namely, the total phase modulation $\phi_{TOT}$ can be controlled so that it is substantially equal to zero by adjusting parameters including the waveforms of the main pulsed light and the sub pulsed light, the length of the first optical fiber 1 and the length of the second optical fiber 2. Consequently, broadening of the wavelength spectrum of the main pulsed light can be suppressed.

If the peak intensity of the main pulsed light is sufficiently low relative to the peak intensity of the sub pulsed light at the time point at which the main pulsed light and the sub pulsed light enter the first optical fiber 1, $\phi_{SPM1}$ takes a small value. If $\phi_{SPM1}$ can be regarded as approximately equal to zero ($\phi_{SPM1} \approx 0$), $\phi_1 \approx \phi_{XPM1}$ is also true, and in such a case, equation (1) can be rewritten into equation (2) below.

$$\phi_{TOT} = \phi_{XPM1} + \phi_{SPM2} \quad (2)$$

As explained above, the sign of $\phi_{XPM1}$ and the sign of $\phi_{SPM2}$ are opposite to each other, and thus, if the absolute value of $\phi_{XPM1}$ is equal to the absolute value of $\phi_{SPM2}$, the total phase modulation $\phi_{TOT}$ is zero. In other words, the phase modulation attributable to the SPM occurring as the main pulsed light is amplified at the second optical fiber 2 and the phase modulation occurring in the main pulsed light, attributable to the XPM caused by the sub pulsed light, at the first optical fiber 1 can be made to cancel each other.

In the pulsed light generation device according to the embodiment, pulsed light can be amplified to assure a high intensity while suppressing broadening of the wavelength spectrum.

Second Embodiment

Figure 3:
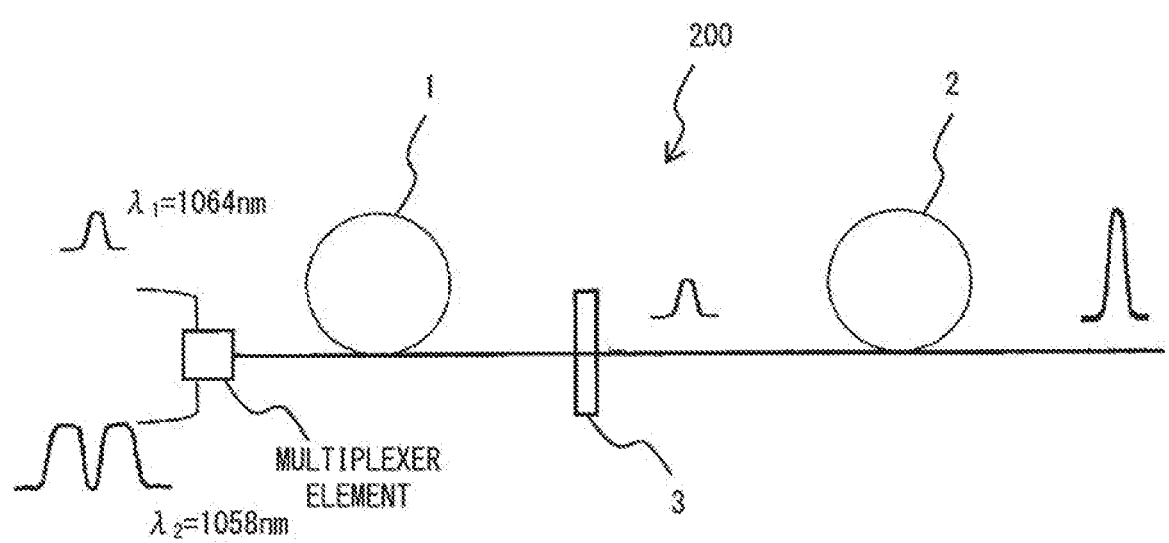
FIG. 3 is a conceptual diagram illustrating the pulsed light generation device according to the second embodiment.

FIG. 3 is a conceptual diagram illustrating a pulsed light generation device 200 according to the second embodiment of the present invention. The pulsed light generation device 200 includes a separation element 3, via which the main pulsed light and the sub pulsed light are separated from each other, disposed between the first optical fiber 1 and the second optical fiber 2. This structure makes it possible to ensure that the sub pulsed light does not enter the second optical fiber 2 by separating the sub pulsed light from the main pulsed light with a high degree of reliability. It is to be noted that in FIG. 3, the same reference signs are assigned to structural components similar to those in the pulsed light generation device 100.

In the pulsed light generation device 200, the main pulsed light and the sub pulsed light assume wavelengths different from each other. For instance, the wavelength of the main pulsed light may be 1064 nm, whereas the wavelength of the sub pulsed light may be 1058 nm. In addition, the peak intensity of the main pulsed light is around 10 mW and the peak intensity of the sub pulsed light is around 80 W. In other words, the peak intensity of the sub pulsed light is much higher than the peak intensity of the main pulsed light, so that an intensity ratio of around 8000:1 is achieved. The first optical fiber 1 may be a single mode optical fiber, the main constituent of which is silica glass. The second optical fiber 2 may be a YDFA (Ytterbium Doped Fiber Amplifier) which is an optical fiber amplifier to amplify light with 1064 nm wavelength. A wavelength selection filter (band-pass filter) 3, which allows the main pulsed light with 1064 nm wavelength to be transmitted but does not allow the sub pulsed light with 1058 nm wavelength to be transmitted, is disposed to function as the separation element between the first optical fiber 1 and the second optical fiber 2.

The main pulsed light of 1064 nm wavelength and the sub pulsed light of 1058 nm wavelength are multiplied and then enter the first optical fiber 1 to be propagated through the first optical fiber 1. In the first optical fiber 1, the phase modulation $\phi_{XPM1}$, attributable to XPM caused by the sub pulsed light, occurs in the main pulsed light. The phase modulation $\phi_{SPM1}$, attributable to SPM, which occurs in the main pulsed light at the first optical fiber 1, takes a small enough value to be disregarded, since the peak intensity of the main pulsed light is extremely low at 10 mW. The main pulsed light and the sub pulsed light having exited the first optical fiber 1 then enter the band-pass filter 3. As explained above, the band-pass filter 3 allows the main pulsed light of 1064 nm wavelength to be transmitted but does not allow the sub pulsed light of 1058 nm wavelength to be transmitted. Thus, the sub pulsed light of 1058 nm wavelength is absorbed or reflected by the band-pass filter 3, and the main pulsed light of 1064 nm wavelength alone enters the second optical fiber 2.

While the main pulsed light having entered the second optical fiber 2 is amplified as it is propagated through the second optical fiber 2, the phase modulation $\phi_{SPM2}$, attributable to SPM, occurs in the main pulsed light. Since the intensities of the main pulsed light and the sub pulsed light change oppositely to each other with time, the phase modulation $\phi_{XPM1}$ and the phase modulation $\phi_{SPM2}$ bear signs opposite to each other. Accordingly, the total phase modulation can be controlled so that it is substantially equal to zero by adjusting the length of the first optical fiber 1 and the length of the second optical fiber 2 so as to allow the phase modulation $\phi_{XPM1}$ and the phase modulation $\phi_{SPM2}$ to cancel each other, which ultimately makes it possible to amplify the main pulsed light while suppressing broadening of the wavelength spectrum. It is to be noted that since the peak intensity of the amplified main pulsed light is set in the specifications, the length of the second optical fiber 2 is firstly determined based on the specifications. Once the length of the second optical fiber 2 has been determined, the phase modulation $\phi_{SPM2}$ can be calculated, and subsequently, the length of the first optical fiber 1 can be set so as to allow the phase modulation $\phi_{XPM1}$ and the phase modulation $\phi_{SPM2}$ to cancel each other.

While the separation element in the pulsed light generation device 200 is constituted with the band-pass filter 3 in the description provided above, a separation element constituted with elements such as a dichroic mirror or a dichroic prism may be used instead.

(Simulation)

Figure 4:
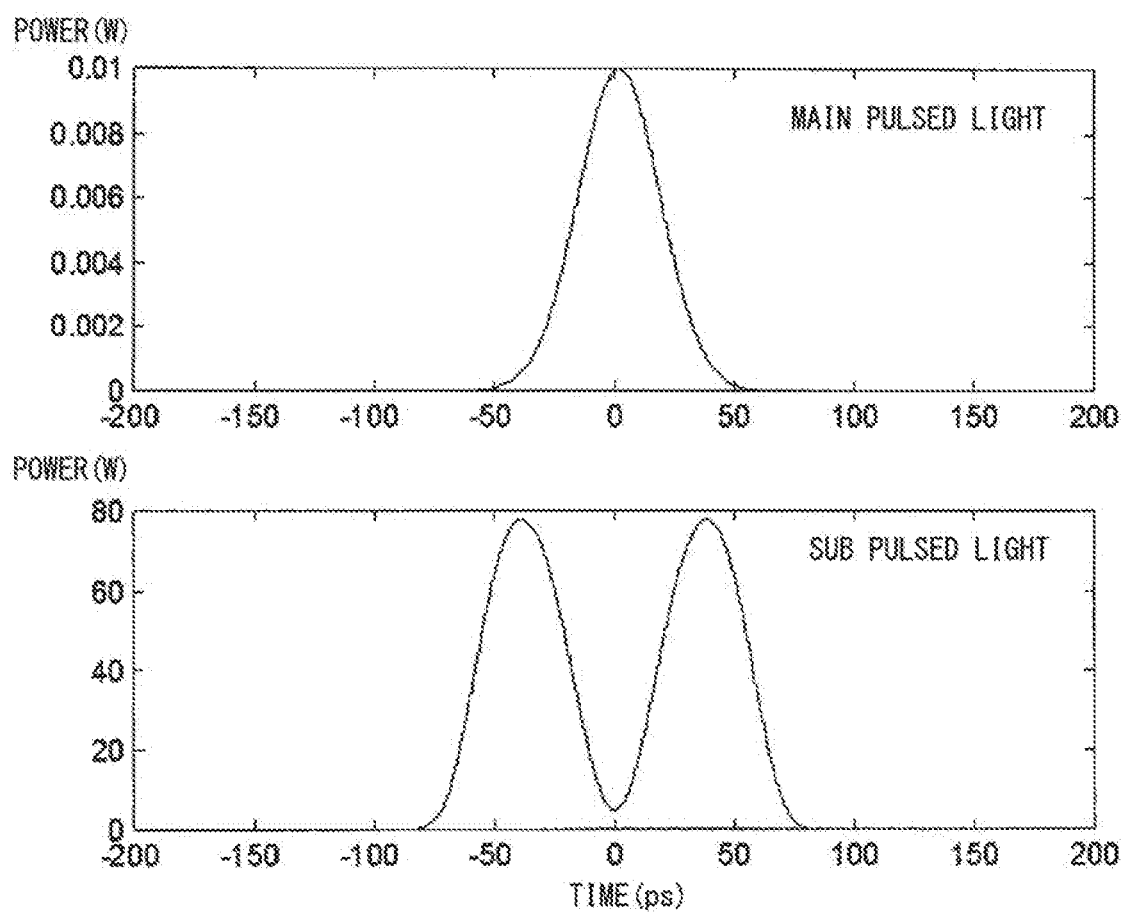
FIG. 4 shows schematic diagrams presenting the waveforms of main pulsed light and sub pulsed light used in a simulation.

Simulation results pertaining to wavelength spectrum broadening are explained next. FIG. 4 shows schematic diagrams presenting the waveforms (intensity changings with time) of the main pulsed light and the sub pulsed light used in the simulation. The top diagram shows the waveform of the main pulsed light, whereas the bottom diagram shows the waveform of the sub pulsed light. The vertical axis on which the intensity of the main pulsed light is indicated, is scaled up by a factor of 8000 relative to the scale of the vertical axis indicating the intensity of the sub pulsed light. The wavelength, the peak intensity and the pulse duration of the main pulsed light are respectively 1064 nm, 10 mW (0.01 W) and 40 ps. The wavelength and the peak intensity of the sub pulsed light are respectively 1058 nm and 80 W. In other words, the peak intensity of the sub pulsed light is far higher than the peak intensity of the main pulsed light with the peak intensity of the sub pulsed light 8000 times that of the main pulsed light.

As FIG. 4 clearly indicates, sub pulsed light is constituted with a pair of pulses and intensity of the central part changes with time along a direction opposite to the direction along which the intensity of the main pulsed light changes with time. Namely, the intensity of the sub pulsed light decreases while the intensity of the main pulsed light increases, and the intensity of the sub pulsed light increases while the intensity of the main pulsed light decreases. The main pulsed light and the sub pulsed light are synchronized so that the intensity of the sub pulsed light peaks at time points both before (preceding) and after (following) the time point at which the intensity of the main pulsed light peaks.

The first optical fiber 1 is assumed to have a length of 20 m, a mode field diameter (MFD) of 6.6 μm, a nonlinear refractive index $n_2=3.0\times10^{-20}$ m$^2$/W, and a dispersion $\beta_2=0.02$ ps$^2$/m. The broadening of the wavelength spectrum of the main pulsed light propagated through the first optical fiber 1 is now analyzed. The propagation of pulsed light through an optical fiber can be expressed with a nonlinear Schrödinger equation of known art. By taking into consideration only the nonlinear refractive index $n_2$ and the dispersion $\beta_2$, the propagation of a slowly varying amplitude $A(z,t)$ of pulsed light can be expressed as in equation (3) below.

$$\frac{\partial A(z,t)}{\partial z} = -i\frac{\beta_2}{2}\frac{\partial^2 A(z,t)}{\partial t^2} + i\gamma|A(z,t)|^2 A(z,t) \quad (3)$$

-continued here, $$\gamma = 2\pi n_2/\lambda A_{\mathit{eff}} = 5.2\times 10^{-3}/\text{W}\cdot\text{m}$$

In addition, $A_{\mathit{eff}}$ in the equation represents the mode cross-sectional area of the first optical fiber 1 and z represents a coordinate set along the optical fiber.

The amplitudes of the main pulsed light and the sub pulsed light at the time point at which they enter the first optical fiber 1 can be expressed as in equation (4) below.

$$A(z=0,t)=A_1(z=0,t)+A_2(z=0,t)\exp(-i\omega_0 t) \quad (4)$$

$A_1$ and $A_2$ in the equation respectively represent the envelope of the main pulsed light and the envelope of the sub pulsed light, whereas $\omega_0$ represents the difference between the frequency of the main pulsed light and the frequency of the sub pulsed light. It is assumed that no phase modulation has occurred (no chirp has occurred) in both of the main pulsed light and the sub pulsed light at the time point at which they enter the first optical fiber 1 and that $A_1$ and $A_2$ are both real numbers.

Figure 5:
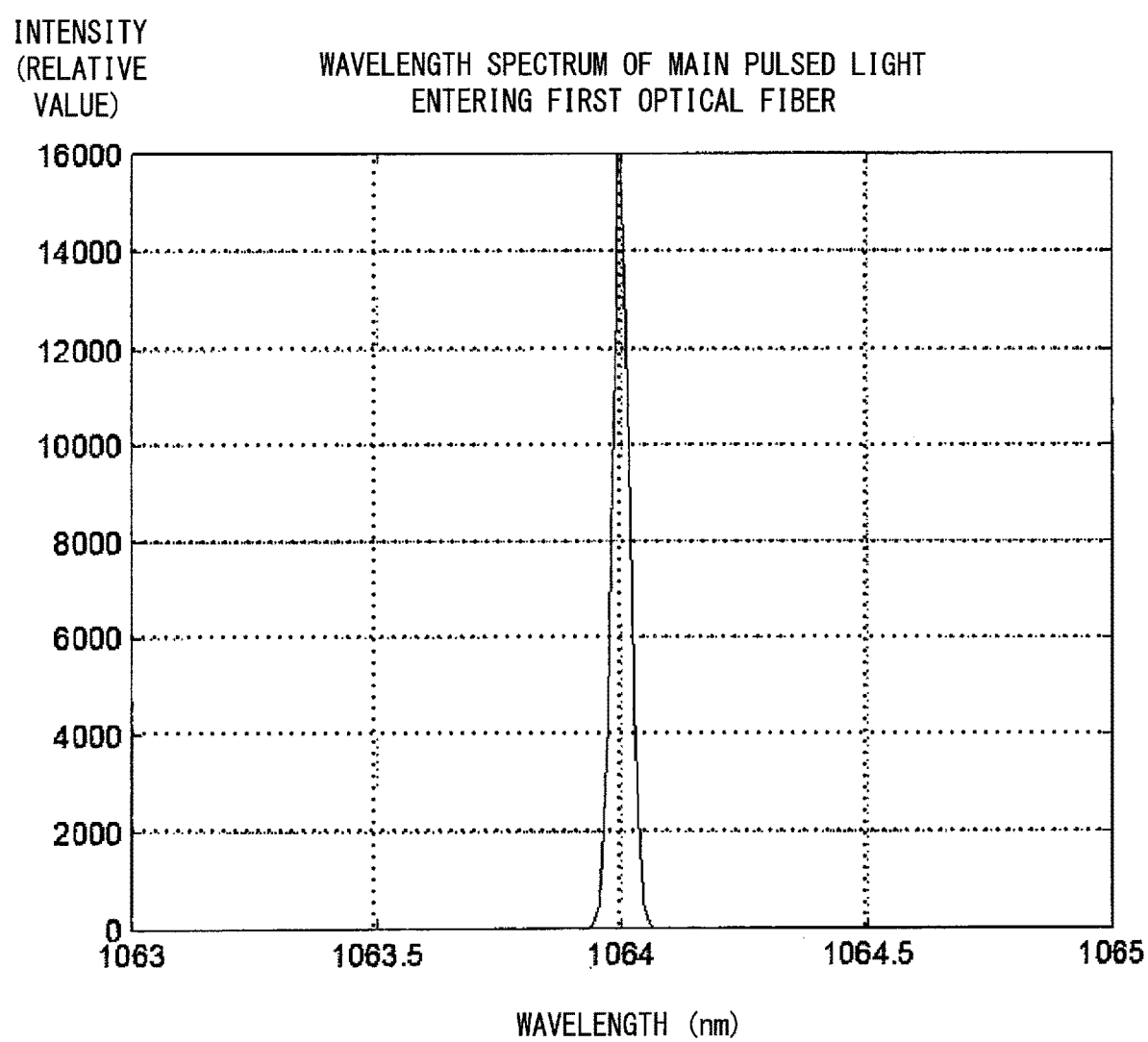
FIG. 5 is a graph of the wavelength spectrum of the main pulsed light entering the first optical fiber in the simulation.

FIG. 5 is a graph showing the main pulsed light wavelength spectrum of the main pulsed light at the time point of entering the first optical fiber 1 in the simulation. The main pulsed light is a transform-limit pulse, and its wavelength spectral width is around 35 pm (0.035 nm). The frequency spectrum of the main pulsed light propagated through the first optical fiber 1 is calculated through Z-direction integration executed by inputting equation (4) in equation (3).

Figure 6:
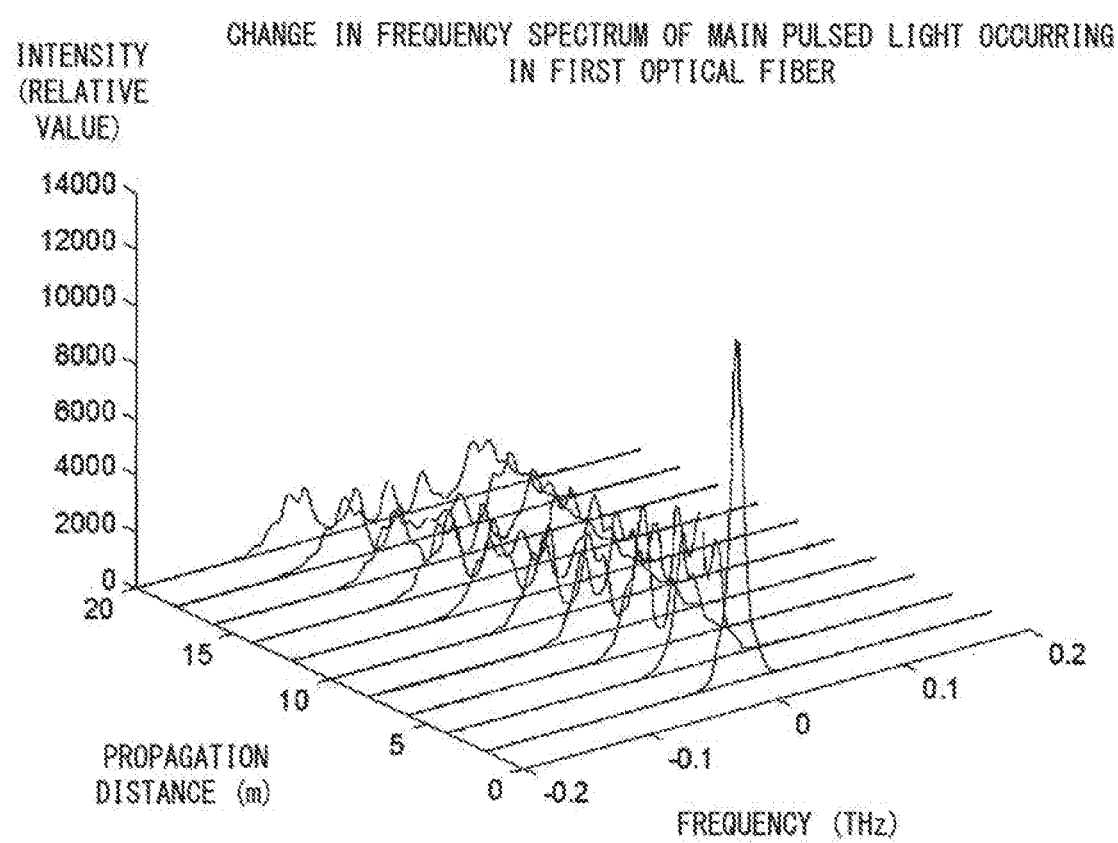
FIG. 6 is a graph presenting simulation results for the frequency spectrum of the main pulsed light propagating through the first optical fiber.

FIG. 6 is a graph showing, in 2 m increments, the frequency spectrum of the main pulsed light propagated through the first optical fiber 1, calculated as described above. FIG. 6 indicates that the frequency spectrum of the main pulsed light becomes broader as the main pulsed light is propagated through the first optical fiber 1. Broadening of the frequency spectrum is equivalent to broadening of the wavelength spectrum width. Such broadening of the frequency spectrum implies that phase modulation has occurred in the main pulsed light due to XPM caused by the sub pulsed light, resulting in broadening of the frequency spectrum of the main pulsed light. It is to be noted that hardly any broadening attributable to SPM occurs in the frequency spectrum (wavelength spectrum) of the main pulsed light at the first optical fiber 1, since the peak intensity of the main pulsed light entering the first optical fiber 1 is sufficiently low, only an extremely low degree of phase modulation attributable to SPM occurs.

The main pulsed light and the sub pulsed light having exited the first optical fiber 1 then enter the band-pass filter 3. Only the main pulsed light is transmitted through the band-pass filter 3. The main pulsed light, having exited the band-pass filter 3, enters the second optical fiber 2 where it is amplified as it propagates. A change occurring in the frequency spectrum, attributable to SPM in the main pulsed light propagated through the second optical fiber 2, is calculated as follows. It is assumed that the second optical fiber 2 has a length of 3 m, a mode field diameter of 20 m, a nonlinear refractive index $n_2=3.0\times10^{-20}$ m$^2$/W and a dispersion $\beta_2=0.02$ ps$^2$/m. For purposes of simplification, the amplification process is not taken into consideration in the calculation, and the peak intensity of the main pulsed light in the second optical fiber 2 is assumed to be constant at 9.2 kW. Under these circumstances, the nonlinear phase modulation is calculated to be 15.7 rad. The maximum value for the nonlinear phase modulation $\phi_{SPM2}$ attributable to SPM is given as $\gamma_2 P_m L_2$, provided that the peak intensity is constant. Here, $\gamma_2$ and $L_2$ respectively represent the nonlinearity and the length of the second optical fiber 2, and $P_m$ represents the peak intensity of the main pulsed light. The nonlinear phase modulation calculated to take a value of 15.7 rad as described above is approximately equal to the value of nonlinear phase modulation occurring when pulsed light with peak intensity of 0.01 W is amplified to achieve a peak intensity of 15 kW by using the optical fiber described above.

The second optical fiber 2 may be constituted with a plurality of optical fibers. Namely, the second optical fiber 2 may be constituted with a plurality of optical fibers (optical fiber elements) disposed in series over a plurality of stages. In this case, the peak intensity of the main pulsed light can be amplified in steps via the optical fiber elements disposed at the plurality of stages instead of amplifying the peak intensity of the main pulsed light from around 0.01 W to around 10 kW through a single second optical fiber 2. For instance, the second optical fiber 2 may be constituted with optical fiber elements disposed in two stages, the peak intensity of the main pulsed light may be amplified from around 0.01 W to around 100 W through the first-stage optical fiber element and the peak intensity may then be amplified to around 10 kW through the second-stage (last stage) optical fiber element. The influence of dispersion is insignificant enough to be disregarded, as long as the pulse duration of the pulsed light is greater than around 40 ps.

It is to be noted that while the second optical fiber 2 is constituted with optical fiber elements disposed in two stages in the explanation provided above, the second optical fiber 2 may be constituted with optical fiber elements disposed in more than two stages. For instance, the intensity of the main pulsed light may be sequentially amplified from around 0.1 W to around 100 W through the optical fiber elements disposed at the first stage and the second stage, and subsequently, the intensity of the main pulsed light may be amplified to around 10 kW through an optical fiber element disposed at a third stage (last stage).

Figure 7:
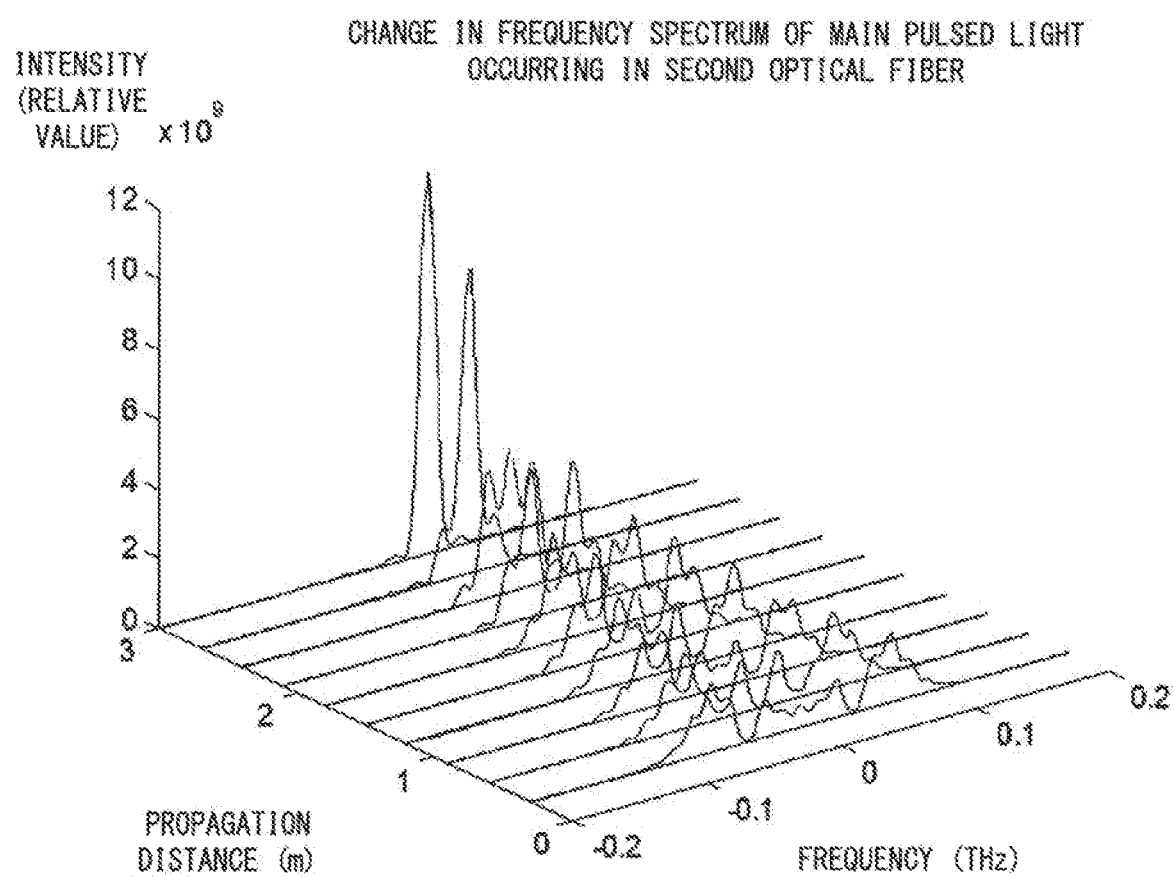
FIG. 7 is a graph presenting simulation results for the frequency spectrum of the main pulsed light propagating through the second optical fiber.

FIG. 7 is a graph showing, in 0.3 m increments, the frequency spectrum of the main pulsed light propagated through the second optical fiber 2, calculated based on equation (3) explained above. FIG. 7 indicates that as the main pulsed light is propagated through the second optical fiber 2, the frequency spectrum of the main pulsed light, which has been broadened, becomes narrower. This is attributable to phase modulation occurring in the main pulsed light through SPM, which reduces the phase modulation having occurred in the main pulsed light at the first optical fiber 1 due to XPM caused by the sub pulsed light.

Figure 8:
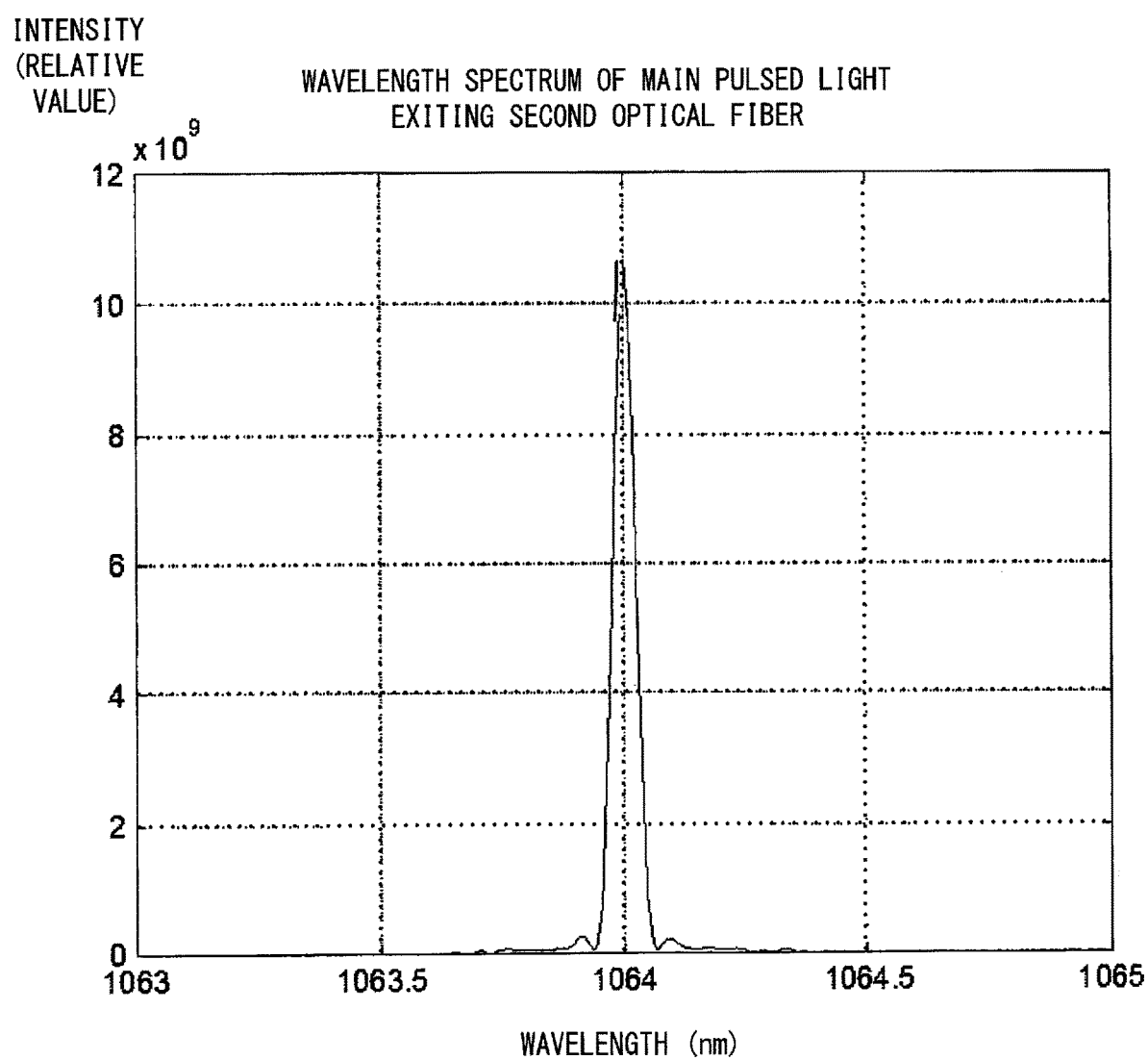
FIG. 8 is a graph presenting simulation results for the wavelength spectrum of the main pulsed light exiting the second optical fiber.

FIG. 8 is a graph showing the wavelength spectrum of the main pulsed light at the time point at which it exits the second optical fiber 2. The wavelength spectrum width is around 55 pm. Considering that the wavelength spectrum of the main pulsed light entering the first optical fiber 1 is 35 pm as indicated in FIG. 5, only an extremely small extent of broadening has occurred in the wavelength spectral width through the amplification of the primary pulsed light. In addition, although not shown, hardly any distortion occurs in the time-waveform of the main pulsed light as it exits the second optical fiber 2. In other words, as not shown, only an extremely small amount of degradation has occurred in the time-waveform of the main pulsed light having passed through the first optical fiber 1 and the second optical fiber 2.

Figure 9:
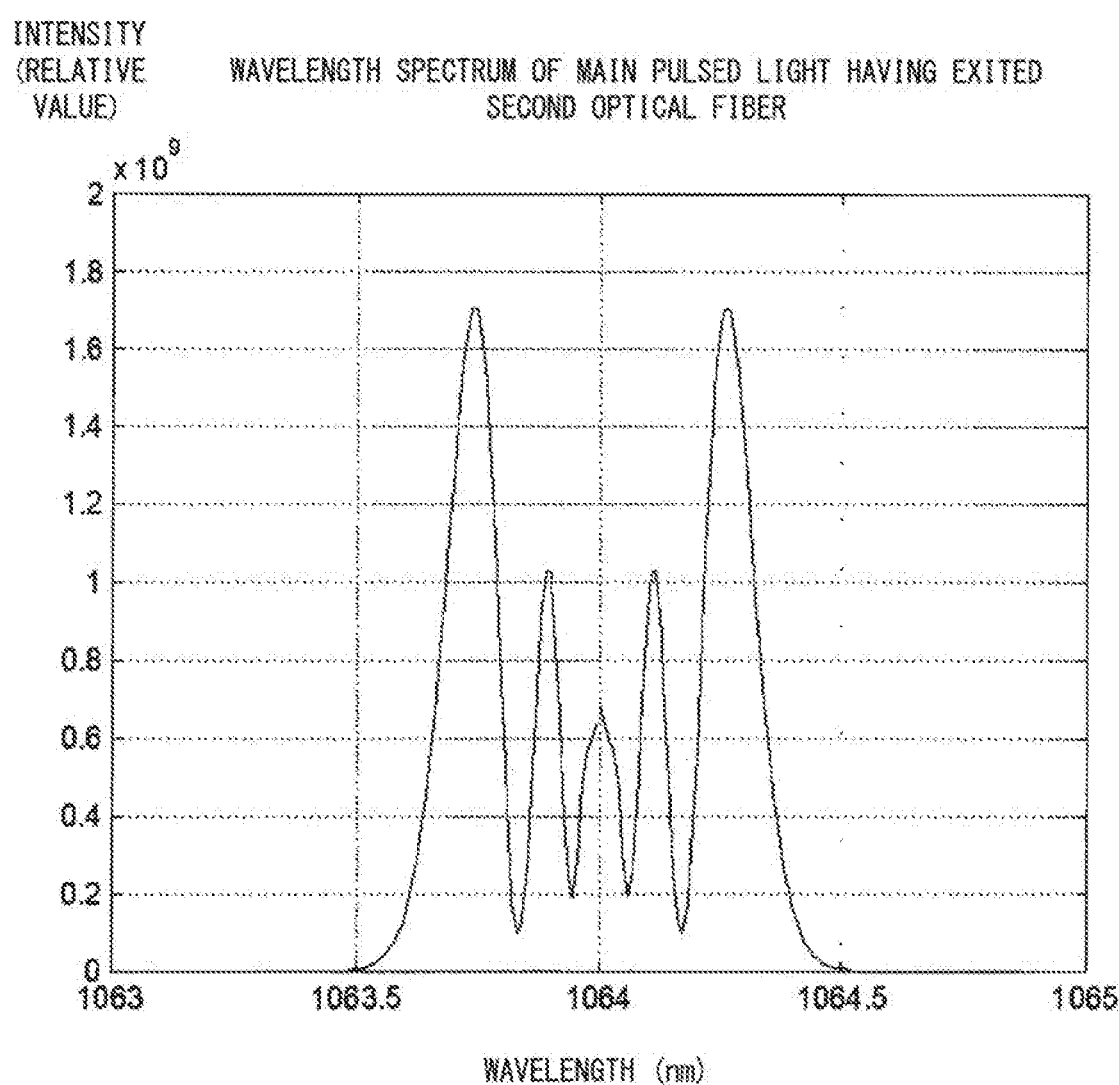
FIG. 9 is a graph presenting simulation results for the wavelength spectrum of the main pulsed light transmitted through a structure that does not include the first optical fiber 1.

For purposes of comparison, FIG. 9 is shown which presents a graph of a wavelength spectrum of the main pulsed light calculated for a device that does not include the first optical fiber 1. As FIG. 9 clearly indicates, if the main pulsed light is amplified only with the second optical fiber 2, the spectral width of amplified main pulsed light becomes markedly broadened to 670 pm. This means that significant phase modulation has occurred in the main pulsed light due to SPM, resulting in significant broadening of the wavelength spectrum of the main pulsed light. Namely, the wavelength spectrum of the main pulsed light is bound to broaden greatly in a device that does not include the first optical fiber 1 having a function of diminishing the phase modulation attributable to SPM, which occurs during amplification.

With respect to the sub pulsed light and the main pulsed light shown in FIG. 4, the absolute value of the phase modulation $\phi_{XPM1}$, attributable to XPM caused by the sub pulsed light on the main pulsed light, is approximately given by $2\gamma_1 P_s L_1$. Here, $\gamma_1$ represents the nonlinearity of the first optical fiber 1 (equation (3)), $P_s$ represents the peak intensity of the sub pulsed light and $L_1$ represents the length of the first optical fiber 1. The value of $\phi_{XPM1}$ can be calculated to be around 16 rad in conjunction with the various parameter values used in the simulation explained above. As has been explained, the nonlinear phase modulation $\phi_{SPM2}$ occurring at the second optical fiber 2 is around 16 rad and thus, $\phi_{SPM2}$ attributable to SPM occurring at the second optical fiber 2 can be diminished or canceled by $\phi_{XPM1}$ attributable to the XPM occurring at the first optical fiber 1. It is to be noted that in comparison to the peak intensity (around 10 kW) of the main pulsed light in the second optical fiber 2, the peak intensity (80 W) of the sub pulsed light in the first optical fiber 1 is markedly lower. Namely, the SPM of the main pulsed light with a high peak intensity can be diminished or canceled with the XPM caused by the sub pulsed light having a lower peak intensity. It is due to the fact that the first optical fiber 1 has a length of 20 m, greater than the length (3 m) of the second optical fiber 2, and the first optical fiber 1 has a mode field diameter of 6.6 μm, smaller than the mode field diameter (20 μm) of the second optical fiber 2.

In addition to the structural components of the pulsed light generation device according to the first embodiment, the pulsed light generation device in this embodiment includes a separation element (wavelength selection filter) 3 via which the main pulsed light and the sub pulsed light are separated from each other. This structure makes it possible to amplify pulsed light so as to achieve a high intensity while suppressing any broadening of the wavelength spectrum and to separate the amplified pulsed light with a high degree of reliability.

Third Embodiment

While the structure according to the second embodiment includes the wavelength selection filter 3 to function as a separation element used to separate the main pulsed light and the sub pulsed light from each other, the main pulsed light and the sub pulsed light can be separated by adopting an alternative structure.

Figure 10:
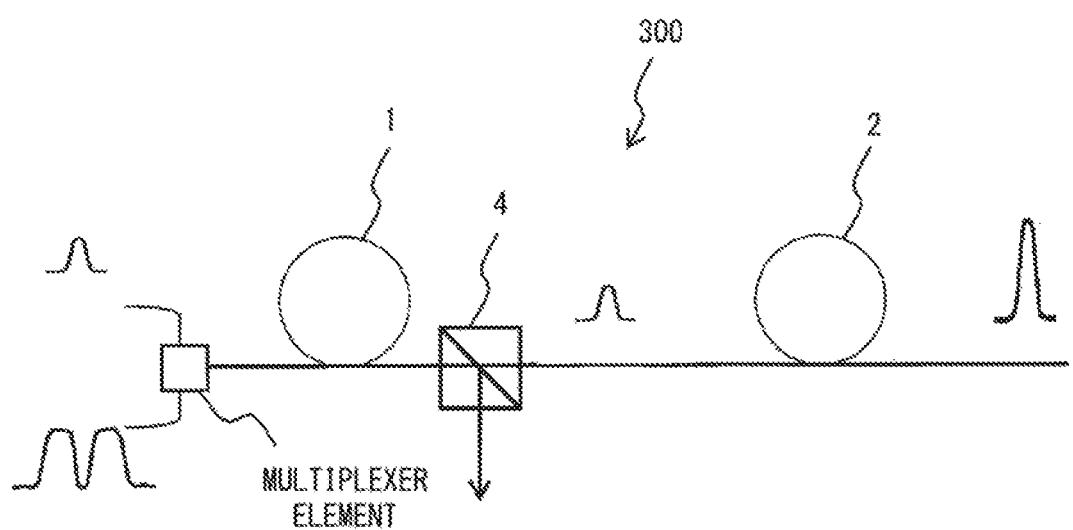
FIG. 10 is a conceptual diagram illustrating the pulsed light generation device according to the third embodiment.

FIG. 10 is a conceptual diagram illustrating a pulsed light generation device 300 according to the third embodiment of the present invention. Main pulsed light and sub pulsed light in the pulsed light generation device 300 are both linearly polarized light, and the polarization direction of the main pulsed light and the polarization direction of the sub pulsed light are different from each other. The polarization direction for the main pulsed light and the polarization direction for the sub pulsed light may be different by, for instance, 90°. The peak intensity of the main pulsed light is 10 mW, whereas the peak intensity of the sub pulsed light is 80 W. The first optical fiber 1 and the second optical fiber 2 are similar to those in the second embodiment. In FIG. 10, the same reference signs are assigned to structural elements similar to those in the pulsed light generation device 200.

A polarization beam splitter 4 is disposed between the first optical fiber 1 and the second optical fiber 2 as a separation element to separate the main pulsed light and the sub pulsed light with their polarization directions different from each other by 90° as described above. The polarization beam splitter 4 is adjusted so that the main pulsed light is transmitted while the sub pulsed light is reflected.

In the pulsed light generation device 300, the main pulsed light and the sub pulsed light having been multiplexed then enter the first optical fiber 1 and are propagated through the first optical fiber 1. The main pulsed light and the sub pulsed light having exited the first optical fiber 1 then enter the polarization beam splitter 4. At the polarization beam splitter 4, the main pulsed light is transmitted toward the second optical fiber 2, whereas the sub pulsed light is reflected along a direction different from the direction in which the main pulsed light is transmitted. As a result, the main pulsed light alone enters the second optical fiber 2. The main pulsed light having entered the second optical fiber 2 is amplified as it is propagated through the second optical fiber 2.

Because it is in the same way as having been described in reference to the second embodiment that the phase modulation of the main pulsed light attributable to SPM, which occurs in the second optical fiber 2, is diminished or canceled by the phase modulation of the main pulsed light attributable to XPM, which occurs at the first optical fiber 1, a repeated explanation is not provided here. In the pulsed light generation device 300 structured as described above, too, the main pulsed light can be amplified without allowing the wavelength spectrum to broaden.

The pulsed light generation device in this embodiment includes a separation element (polarization beam splitter) via which the main pulsed light and the sub pulsed light are separated from each other, in addition to the structural components of the pulsed light generation device according to the first embodiment. By adopting this structure, pulsed light can be amplified to achieve a high intensity while disallowing broadening of the wavelength spectrum, and more reliable separation of the amplified pulsed light can be assured.

Fourth Embodiment

Figure 11:
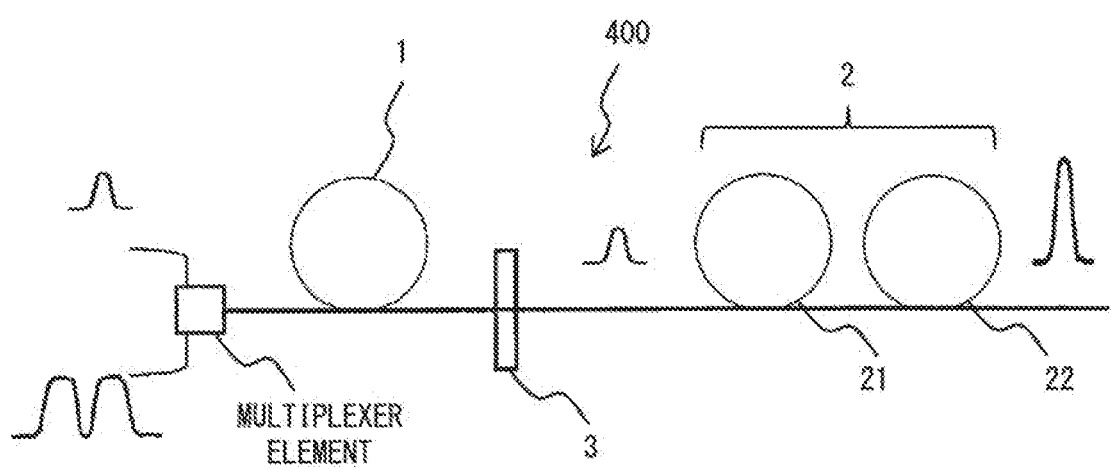
FIG. 11 is a conceptual diagram illustrating the pulsed light generation device according to the fourth embodiment.

FIG. 11 is a conceptual diagram illustrating a pulsed light generation device 400 according to the fourth embodiment of the present invention. The pulsed light generation device 400 is configured by replacing the second optical fiber 2 in the pulsed light generation device 200 with optical fibers (optical fiber elements) disposed in a plurality of stages. Namely, the second optical fiber 2 is constituted with two optical fibers, i.e., a first optical fiber element 21 and a second optical fiber element 22. In the pulsed light generation device 400, the intensity of the main pulsed light is amplified from 0.01 W to around 10 W through the first optical fiber element 21 and is further amplified to around 10 kW through the second optical fiber element 22. By adopting this structure, the main pulsed light can be amplified while disallowing broadening of the wavelength spectrum with an even higher degree of reliability.

The second optical fiber 2 constituted with optical fiber elements disposed in a plurality of stages can be adopted in the pulsed light generation device 300 in the third embodiment, as well.

Fifth Embodiment

Figure 12:
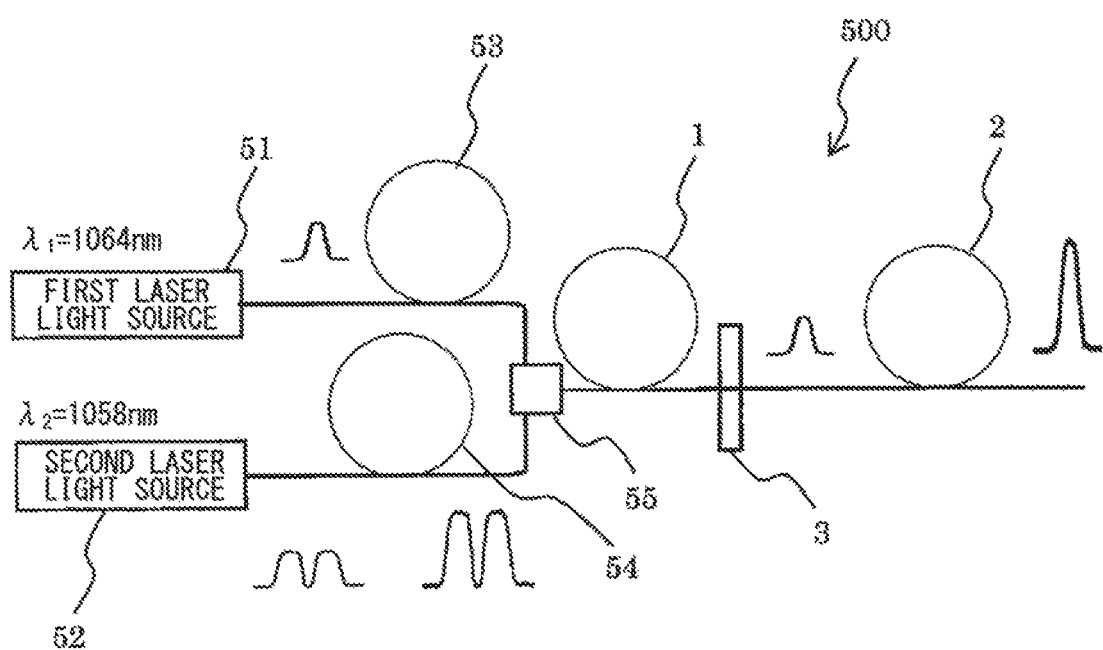
FIG. 12 is a conceptual diagram illustrating the pulsed light generation device according to the fifth embodiment.

FIG. 12 is a conceptual diagram illustrating a pulsed light generation device 500 according to the fifth embodiment of the present invention. The pulsed light generation device 500 includes two laser light sources that emit light with wavelengths different from each other. Main pulsed light is emitted from one of the laser light sources and sub pulsed light is emitted from the other laser light source. The pulsed light generation device 500 includes a first laser light source 51 that emits main pulsed light with a wavelength of 1064 nm and a second laser light source 52 that emits sub pulsed light with a wavelength of 1058 nm. The first laser light source 51 and the second laser light source 52 each include a modulator, and light with the 1064 nm wavelength and the light with the 1058 nm wavelength are individually modulated via the modulators and are emitted as the main pulsed light and the sub pulsed light. The peak intensities of the main pulsed light and the sub pulsed light are both 10 mW.

The pulsed light generation device 500 further includes a third optical fiber 53 through which the main pulsed light having been emitted from the first laser light source 51 is propagated, and a fourth optical fiber 54 through which the sub pulsed light having been emitted from the second laser light source 52 is propagated. The main pulsed light having exited the third optical fiber 53 and the sub pulsed light having exited the fourth optical fiber 54 enter a multiplexer element 55 where they are multiplexed. In the fourth optical fiber 54, the peak intensity of the sub pulsed light is amplified from around 10 mW to around 80 W. The third fiber 53 is disposed for purposes of optical path length adjustment in order to synchronize the main pulsed light with the sub pulsed light at the multiplexer element 55.

"Synchronizing the main pulsed light with the sub pulsed light" means timing adjustment so as to let the intensity of the sub pulsed light decrease while the intensity of the main pulsed light increases and to let the intensity of the sub pulsed light increase while the intensity of the main pulsed light decreases. Namely, the intensity change with time occurring in the main pulsed light and the intensity change with time occurring in the sub pulsed light have a reverse relation to each other. It is to be noted that the fourth optical fiber 54 may be constituted with a single optical fiber or it may be constituted with optical fibers disposed in a plurality of stages.

A first optical fiber 1, a second optical fiber 2 and a band-pass filter 3 are similar to those included in the pulsed light generation device 200 according to the second embodiment. In addition, the main pulsed light and the sub pulsed light, having been multiplexed, enter the first optical fiber 1 in the same way as in the pulsed light generation device 200. The main pulsed light is amplified while disallowing broadening of the wavelength spectrum in the same way as in the pulsed light generation device 200. It is to be noted that the second optical fiber 2 may be constituted with optical fiber elements disposed in a plurality of stages in this embodiment, as well.

The pulsed light generation device in this embodiment includes two laser light sources having an optimal wavelength difference, from which the main pulsed light and the sub pulsed light are individually emitted, and a wavelength selection filter 3 functioning as a separation element via which the main pulsed light and the sub pulsed light are separated from each other. By adopting this structure, pulsed light can be amplified to achieve a high intensity while suppressing broadening of the wavelength spectrum, and more reliable separation of the amplified pulsed light can be assured.

Sixth Embodiment

Figure 13:
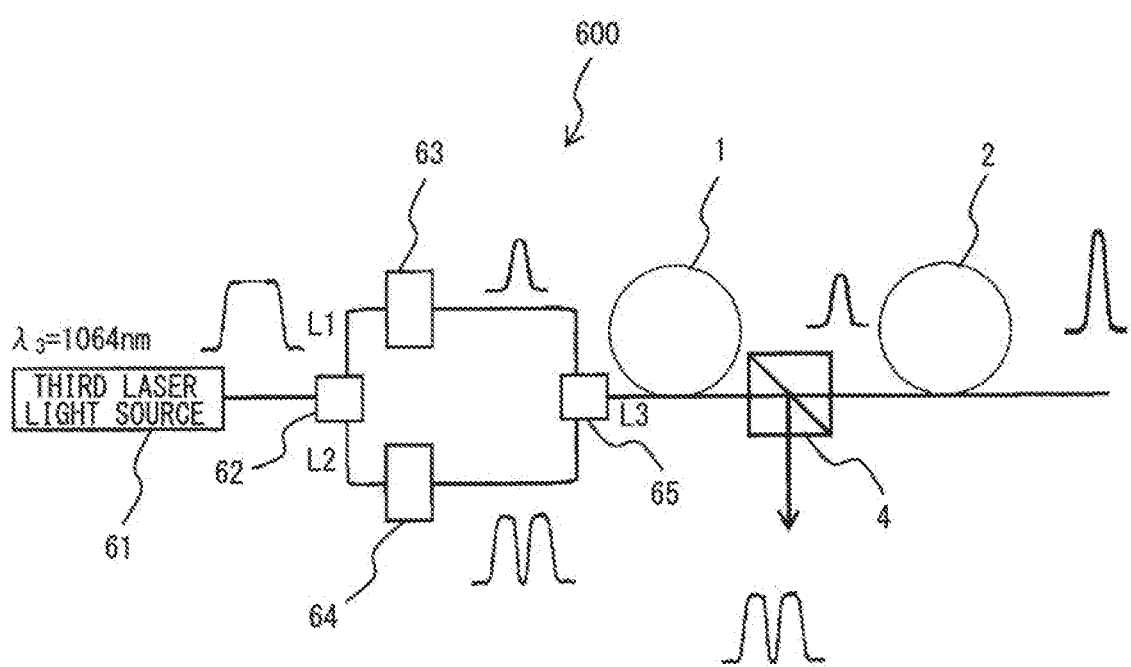
FIG. 13 is a conceptual diagram illustrating the pulsed light generation device according to the sixth embodiment.

FIG. 13 is a conceptual diagram illustrating a pulsed light generation device 600 according to the sixth embodiment of the present invention. The pulsed light generation device 600 includes a third laser light source 61 that emits linearly polarized pulsed light or linearly polarized continuous light with a wavelength of 1064 nm and a demultiplexer element 62 that branches the pulsed light or continuous light having been emitted from the third laser light source into light to be propagated through a first optical path L1 and light to be propagated through a second optical path L2. The pulsed light generation device 600 further includes a first modulation element 63 that is disposed in the first optical path L1 and generates main pulsed light and a second modulation element 64 that is disposed in the second optical path L2 and generates sub pulsed light. The pulsed light generation device 600 further includes a multiplexer element 65 that multiplexes the main pulsed light propagated through the first optical path L1 and the sub pulsed light propagated through the second optical path L2 and allows the multiplexed light to be propagated through a third optical path L3. The demultiplexer element 62 may be a 1:99 branch coupler (with a 1% port connected to the optical path L1 and a 99% port connected to the optical path L2), and the multiplexer element 65 may be constituted with a polarization beam splitter.

In the pulsed light generation device 600, the third laser light source 61 emits linearly polarized pulsed light or linearly polarized continuous light. The pulsed light or continuous light is branched by the demultiplexer element 62 into light to be propagated through the first optical path L1 and light to be propagated through the second optical path L2. The first modulation element 63 and the second modulation element 64 are disposed respectively in the first optical path L1 and in the second optical path L2. The first modulation element 63 modulates the pulsed light being propagated through the first optical path L1 and generates the main pulsed light. The second modulation element 64 modulates the pulsed light being propagated through the second optical path L2 and generates the sub pulsed light. While the first modulation element 63 and the second modulation element 64 may be each constituted with an electro-optic modulator (EO modulator), they may be constituted with modulators other than electro-optic modulators (e.g., acousto-optic modulators or the like).

The main pulsed light and the sub pulsed light are multiplexed by the multiplexer element 65 and are propagated through the third optical path L3, and then they enter the first optical fiber 1. The main pulsed light and the sub pulsed light having been multiplexed are propagated through paths similar to those in the pulsed light generation device 300 according to the third embodiment described in reference to FIG. 10.

The pulsed light generation device according to this embodiment adopts a structure that allows the main pulsed light and the sub pulsed light to be generated from pulsed light emitted from a single laser light source, and that separates the main pulsed light and the sub pulsed light from each other by a polarization beam splitter functioning as a separation element after the main pulsed light and the sub pulsed light are set to have polarization directions different from each other. By adopting this structure, pulsed light can be amplified to achieve a high intensity while disallowing broadening of the wavelength spectrum, and more reliable separation of the amplified pulsed light can be assured.

Seventh Embodiment

Figure 14:
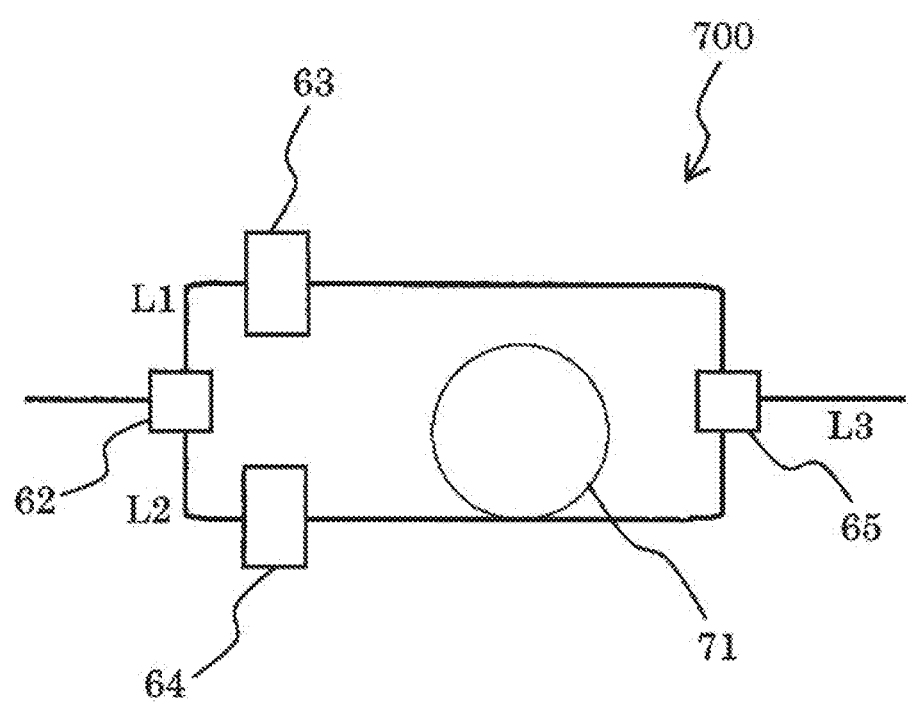
FIG. 14 is a conceptual diagram illustrating the pulsed light generation device according to the seventh embodiment.

FIG. 14 is a conceptual diagram illustrating a pulsed light generation device 700 according to the seventh embodiment of the present invention. The pulsed light generation device 700 further includes a third optical fiber 71 disposed in the second optical path L2, in addition to the structural components in the pulsed light generation device 600. FIG. 14 only shows the structure in the vicinity of the first optical path L1 and the second optical path L2 and does not show a structure in other areas. It is preferred that the peak intensity of the sub pulsed light be sufficiently higher than the peak intensity of the main pulsed light at a time point at which the main pulsed light and the sub pulsed light, having been multiplexed, enter the first optical fiber 1. Accordingly, the pulsed light generation device 700 includes the third optical fiber 71 used to amplify the sub pulsed light, which is disposed in the second optical path L2.

In the pulsed light generation device 700, pulsed light or continuous light emitted from the third laser light source 61 is branched by the demultiplexer element 62 into light to be propagated through the first optical path L1 and light to be propagated through the second optical path L2. The demultiplexer element 62 may be constituted with a 50:50 branch coupler. In the first optical path L1, main pulsed light is generated via the first modulation element 63, and in the second optical path L2, sub pulsed light is generated via the second modulation element 64. At the time of their generation, the main pulsed light and the sub pulsed light both have a peak intensity of around 10 mW. In the second optical path L2, the sub pulsed light is amplified by the third optical fiber 71 so as to achieve a peak intensity of around 80 W. The third optical fiber 71 may be a YDFA, which is an optical fiber amplifier to amplify light with 1064 nm wavelength. The main pulsed light and the sub pulsed light are multiplexed by the multiplexer element 65 and are propagated through the third optical path L3. The multiplexer element 65 may be constituted with a polarization beam splitter. The main pulsed light and the sub pulsed light having been multiplexed are propagated through paths similar to those in the pulsed light generation device 300 according to the third embodiment described in reference to FIG. 10.

The pulsed light generation device 700 according to the seventh embodiment is configured so that the peak intensity of the main pulsed light is set lower than the peak intensity of the sub pulsed light. By adopting this structure, pulsed light can be amplified to achieve a high intensity while suppressing broadening of the wavelength spectrum.

According to the seventh embodiment, the intensity of the pulsed light or continuous light emitted from the third laser light source 61 can be adjusted to an optimal value for subsequent amplification at the second optical fiber 2.

Eighth Embodiment

Figure 15:
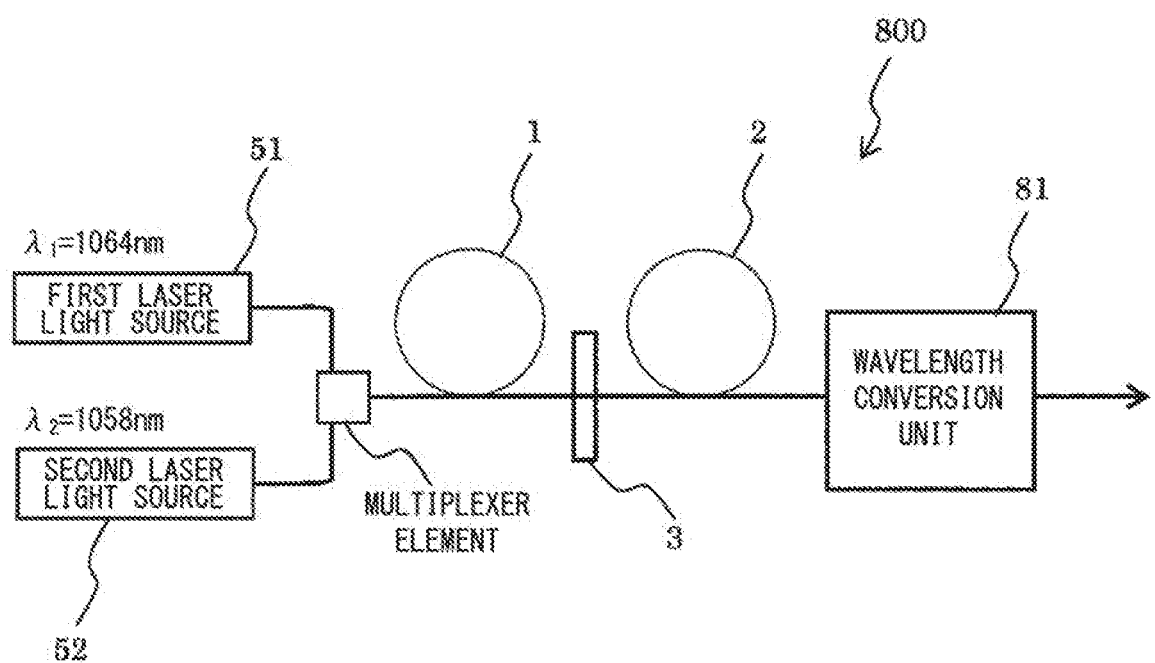
FIG. 15 is a conceptual diagram illustrating the pulsed light generation device according to the eighth embodiment.

FIG. 15 is a conceptual diagram illustrating a pulsed light generation device 800 according to the eighth embodiment of the present invention. In the pulsed light generation device 800, the wavelength of the amplified main pulsed light having exited the second optical fiber 2 is converted to a shorter wavelength. The pulsed light generation device 800 is configured so as to further include a wavelength conversion unit 81 disposed on the downstream side relative to the second optical fiber 2, in addition to the structural components in the pulsed light generation device 500. The main pulsed light, having been propagated and amplified through the second optical fiber 2, enters the wavelength conversion unit 81. The wavelength conversion unit 81 includes a plurality of nonlinear optical crystals, which converts the wavelength of the main pulsed light to a wavelength in the ultraviolet range and emits the wavelength converted main pulsed light. Namely, the pulsed light generation device 800 outputs ultraviolet pulsed light.

Figure 16:
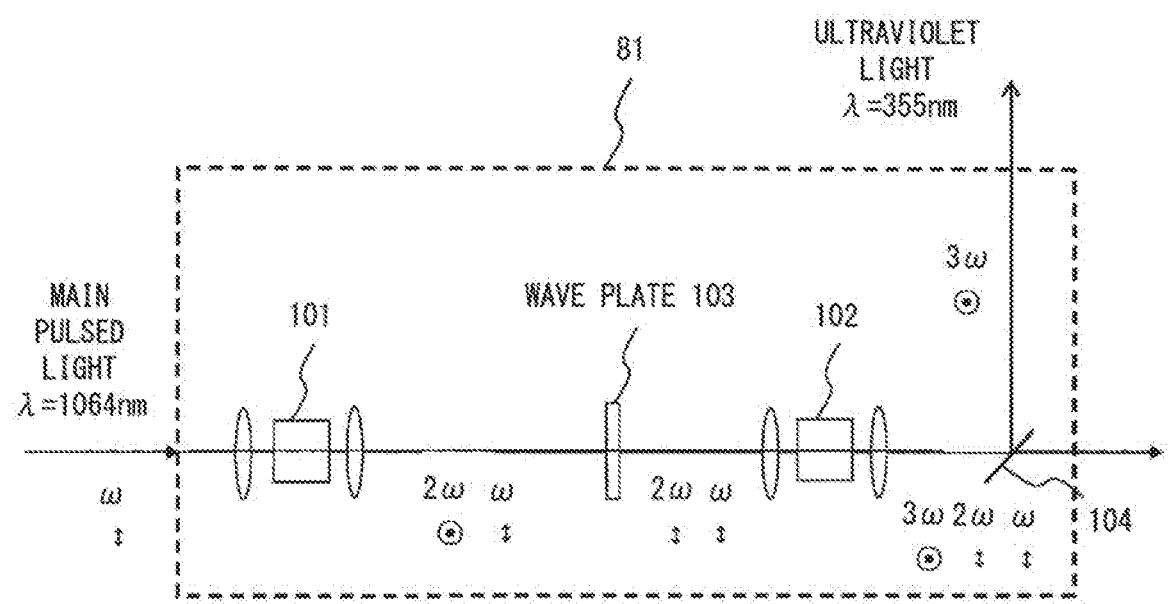
FIG. 16 is a schematic diagram presenting an example of a specific structure that may be adopted in the wavelength conversion unit.

FIG. 16 is a schematic diagram presenting a specific structure that may be adopted for the wavelength conversion unit 81. In FIG. 16, an arrow pointing up/down represents linearly polarized light, polarized along a direction parallel to the sheet (P polarization), and a double circle mark represents linearly polarized light, polarized along a direction perpendicular to the sheet (S polarization). In addition, each vertically elongated ellipsoid represents a lens used to shape the main pulsed light, and ω represents the frequency of the main pulsed light. The main pulsed light with the 1064 nm wavelength having exited the second optical fiber 2 enters the wavelength conversion unit 81. The main pulsed light at the time point of entering the wavelength conversion element 81 is P polarized light.

The main pulsed light (hereafter may be referred to as a fundamental wave) of P polarization having entered the wavelength conversion unit 81, enters a nonlinear optical crystal 101 and is propagated therethrough, and second harmonic of the fundamental wave of S polarization with a frequency 2ω is generated. The nonlinear optical crystal 101 may be, for instance, an LBO crystal. The second harmonic of S polarization, having been generated at the nonlinear optical crystal 101, and the fundamental wave of P polarization, having been transmitted through the nonlinear optical crystal 101, enter a wave plate 103. At the wave plate 103, the polarization direction of the second harmonic is altered by 90° and thus, the second harmonic of S polarization is converted to the second harmonic of P polarization. The second harmonic of P polarization and the fundamental wave of P polarization enter a nonlinear optical crystal 102 and are propagated therethrough. At the nonlinear optical crystal 102, third harmonic of S polarization (with a frequency 3ω) is generated through sum-frequency generation. The nonlinear optical crystal 102 may be an LBO crystal.

The third harmonic of S polarization, having been generated at the nonlinear optical crystal 102, and the fundamental wave of P polarization, having been transmitted through the nonlinear optical crystal 102, enter a dichroic mirror 104. At the dichroic mirror 104, the third harmonic of S polarization alone is reflected while the second harmonic of P polarization and the fundamental wave of P polarization are transmitted through. As a result, the third harmonic of S polarization is separated. The wavelength of the third harmonic is 355 nm in the ultraviolet range.

While the main pulsed light that enters the wavelength conversion unit 81 is the light of P polarization in the example described above, the main pulsed light of S polarization may instead enter the wavelength conversion unit 81 and, also in such a case, the main pulsed light with wavelength in the ultraviolet range can be obtained through the configuration illustrated in FIG. 16.

It is to be noted that while the configuration according to the eighth embodiment includes the wavelength conversion unit 81 added to the pulsed light generation device 500, a configuration that includes the wavelength conversion unit 81 added to the pulsed light generation device 600, 700 or 800 may be adopted instead.

In the pulsed light generation device according to this embodiment, the main pulsed light can be amplified so as to achieve a high intensity while disallowing broadening of the wavelength spectrum, and furthermore, the wavelength of the main pulsed light can be converted to a wavelength in the ultraviolet range. Such a pulsed light generation device can preferably be used as a light source for an exposure apparatus, an inspection apparatus or the like for manufacturing a high-density integrated circuit.

Figure 17:
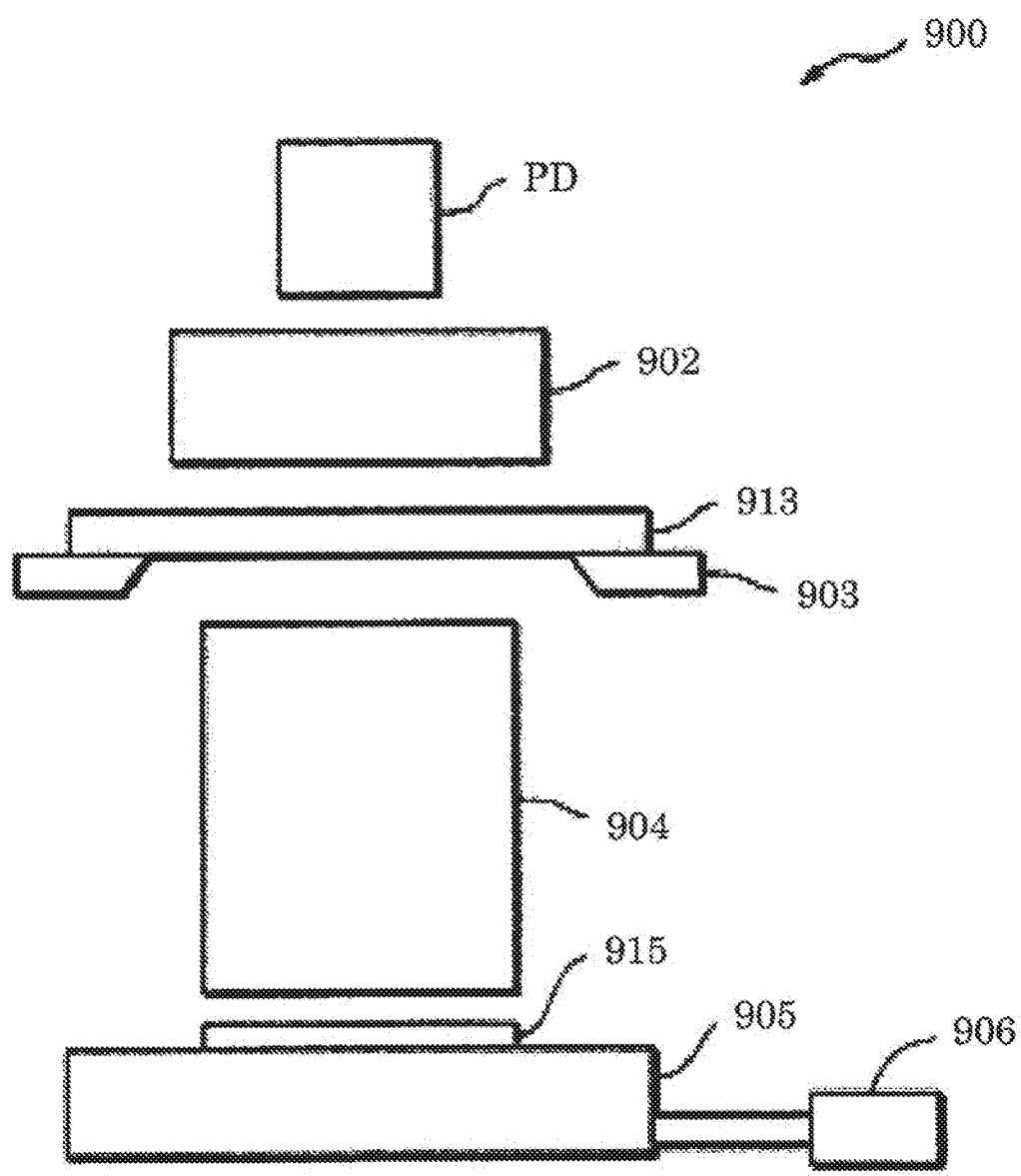
FIG. 17 is a diagram schematically illustrating the configuration of an exposure apparatus, representing a first application example of a system having a pulsed light generation device.

An exposure apparatus used in a photolithography process in manufacturing of semiconductor or liquid crystal panel, as a first application example of a system equipped with the pulsed light generation device described above, will now be explained in reference to FIG. 17 schematically illustrating its structure. In an exposure apparatus 900, a fine pattern drawn on a photomask 913 constituted of silica glass, which functions as a pattern forming unit, is transferred by optically projecting the pattern onto an exposure target 915, such as a semiconductor wafer or a glass substrate having a photo resist applied thereto, through a process that is, in principle, similar to a photo engraving process.

The exposure apparatus 900 is configured to include the above-described pulsed light generation device PD (e.g., the pulsed light generation device 800), an illumination optical system 902, a mask support stage 903 which holds the photomask 913, a projection optical system 904, an exposure target support table 905 which holds the exposure target 915, and a drive mechanism 906 which moves the exposure target support table 905 in a horizontal plane. The illumination optical system 902 includes a plurality of lens groups and irradiates an ultraviolet pulsed light output from the pulsed light generation device PD onto the photomask 913 which is held on the mask support stage 903. The projection optical system 904 includes a plurality of lens groups and projects the light transmitting through the photomask 913 onto the exposure target 915 held on the exposure target support table.

In the exposure apparatus 900, the ultraviolet pulsed light output from the pulsed light generation device PD is input to the illumination optical system 902 and adjusted to have a predetermined light flux. The ultraviolet pulsed light flux is then irradiated onto the photomask 913 which is held at the mask support stage 903. An image of the pattern drawn on the photomask 913 is formed at a predetermined position of the exposure target 915 which is held on the exposure target support table 905 via the projection optical system 904. Through this process, an image of the pattern on the photomask 913 is exposed onto the exposure target 915, such as a semiconductor wafer or a glass substrate for a liquid crystal panel, at a predetermined magnification factor.

The exposure apparatus 900 is equipped with the pulsed light generation device PD of a relatively simple structure, capable of providing a high output and outputting ultraviolet pulsed light with a high-quality beam. Thus, it may be expected to contribute to an improvement of the throughput in the photolithography process and to an improvement in the processing quality.

Figure 18:
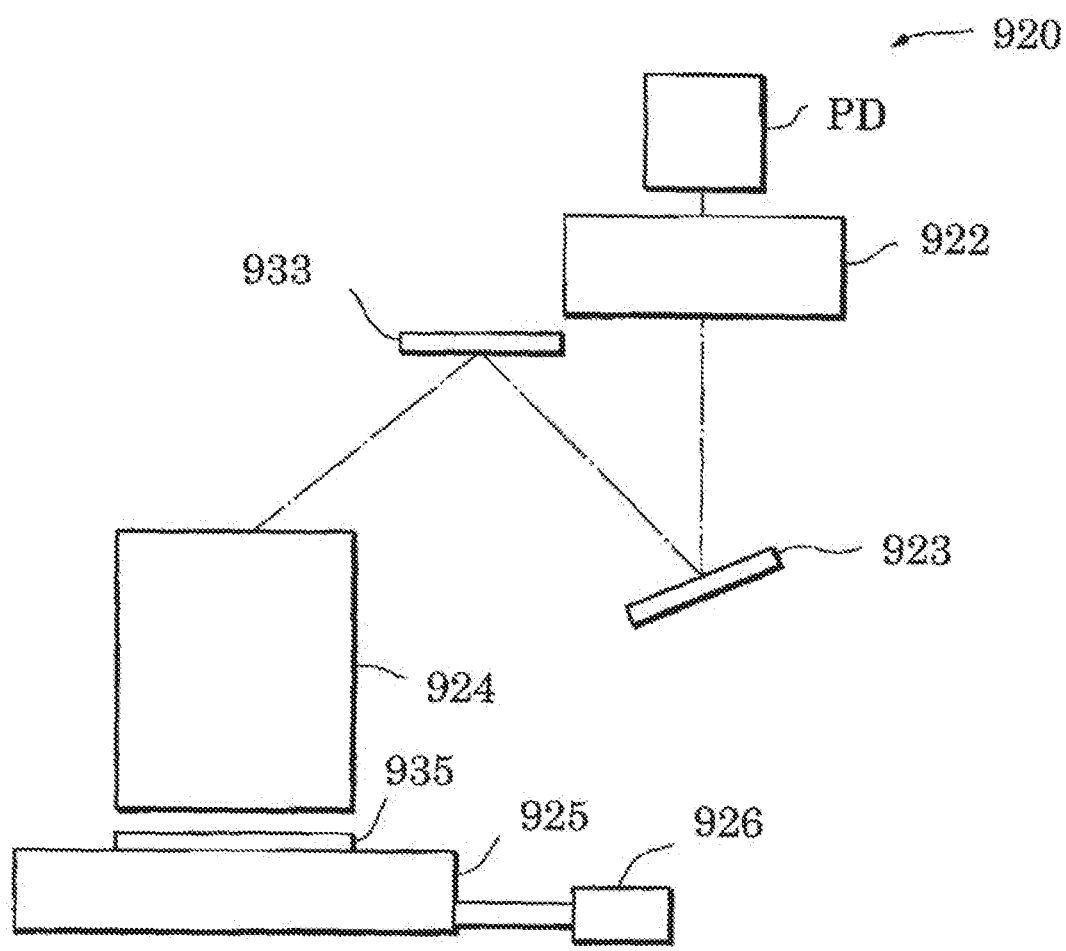
FIG. 18 is a diagram schematically illustrating the configuration of an exposure apparatus, representing a second application example of a system having a pulsed light generation device.

An exposure apparatus that includes a variable pattern forming mask to function as a pattern forming unit, as a second application example of a system equipped with the pulsed light generation device described above will be explained next in reference to FIG. 18, schematically illustrating its structure. An exposure apparatus 920 is similar to the exposure apparatus 900 in the first application example explained above, except that it includes a variable pattern forming mask instead of the photomask. In the exposure apparatus 920, an image of an arbitrary pattern, generated by the variable pattern forming mask, is transferred by optically projecting onto an exposure target 935, such as a glass substrate or a semiconductor wafer with a photoresist applied thereto (see, for instance, Japanese Patent Publication No. 5211487, Japanese Laid Open Patent Publication No. 2012-54500, Japanese Laid Open Patent Publication No. 2011-49296, all submitted by the applicant of the present invention).

The exposure apparatus 920 comprises a pulsed light generation device PD described above (e.g., the pulsed light generation device 800), an illumination optical system 922, a variable pattern forming mask 933, a projection optical system 924, an exposure target support table 925 at which the exposure target 935 is held, and a drive mechanism 926 that drives the exposure target support table 925 in a horizontal plane. Via the illumination optical system 922 constituted with a plurality of lens groups, the variable pattern forming mask 933 via a mirror 923 is irradiated with ultraviolet pulsed light output from the pulsed light generation device PD. Via the projection optical system 924 constituted with a plurality of lens groups, light carrying arbitrary pattern formed by the variable pattern forming mask 933 is projected onto the exposure target 935 placed on the exposure target support table 925.

The variable pattern forming mask 933 is structured with a plurality of movable mirrors so as to generate reflected light in arbitrary pattern. A DMD (digital micro-mirror device or deformable micromirror device) configured by disposing a plurality of movable mirrors in a two-dimensional pattern, is an preferable example of such a variable pattern forming mask 933. Each of the movable mirrors are disposed so that their reflecting surfaces can be adjusted to turn along desired directions independently, and each movable mirror is switched between an ON position and an OFF position by a DMD drive device (not shown). As an alternative, the pattern forming unit may be a micromirror device that switches the reflected light between an ON state and an OFF state simply by creating a phase shift in reflected light without altering the orientation of the reflecting surface of each movable mirror.

Upon the DMD drive device controls the position of a movable mirrors so that they take the ON position, light having exited the illumination optical system 922 is reflected by the movable mirrors, enters the projection optical system 924 and forms an image on the exposure surface of the exposure target 935. On the other hand, upon the DMD drive device controls the position of a movable mirror so that it takes an OFF position, light having exited the illumination optical system 922 is reflected at the movable mirrors but does not enter the projection optical system 924 and instead, it is absorbed into a damper disposed on the optical path of the reflected light. Accordingly, exposure can be executed with light in arbitrary pattern, by controlling movable mirrors disposed at predetermined positions so that they are set in the ON position and controlling other movable mirrors so that they are set in the OFF position.

In the exposure apparatus 920, the ultraviolet pulsed light output from the pulsed light generation device PD enters the illumination optical system 922 and it is adjusted into a predetermined light flux and the variable pattern forming mask 933 is irradiated with the ultraviolet pulsed light via the mirrors 923. The ultraviolet pulsed light formed in a predetermined pattern by the variable pattern forming mask 933 enters the projection optical system 924 and then a predetermined position of the exposure target 935 held at the exposure target support table 925 is irradiated with the ultraviolet pulsed light. Through this process, an image is formed with exposure light corresponding to the exposure pattern on the exposure target 935 such as a semiconductor wafer or a liquid crystal panel at a predetermined magnification factor.

As explained above, the pulsed light generation device PD is capable of high speed ON/OFF control of ultraviolet pulsed light. This means that the ultraviolet pulsed light, which is a particularly crucial factor in an exposure apparatus including a variable pattern forming mask, can be controlled with high accuracy. This makes it possible to achieve highly accurate exposure.

Figure 19:
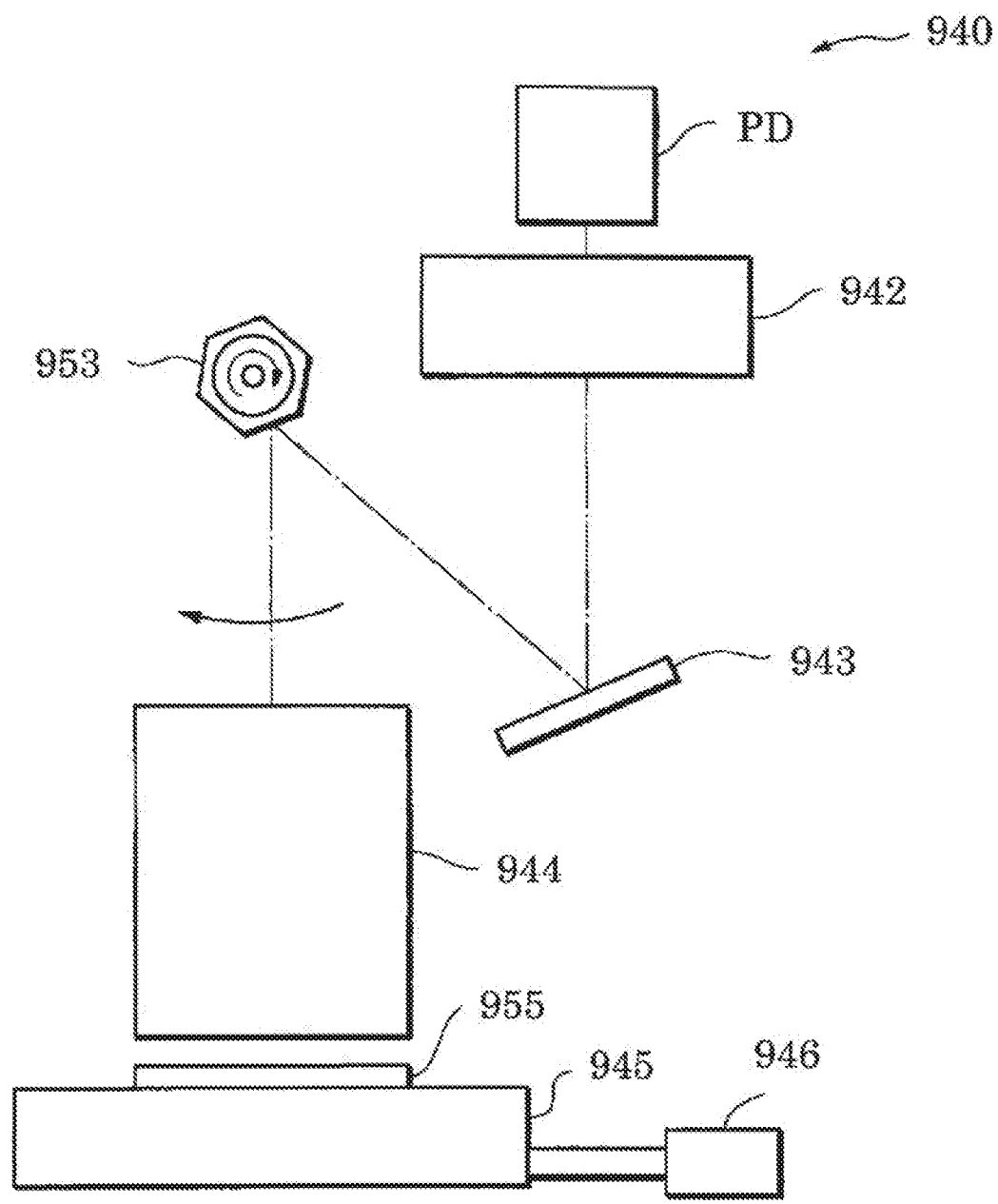
FIG. 19 is a diagram schematically illustrating the configuration of an exposure apparatus, representing a third application example of a system having a pulsed light generation device.

An exposure apparatus that adopts a direct drawing system as a third application example of a system equipped with the pulsed light generation device described above will be explained next in reference to FIG. 19. A pattern forming unit of this exposure apparatus 940 directly draws an image of arbitrary pattern set in advance by deflecting ultraviolet pulsed light output from the pulsed light generation device PD so that ultraviolet pulsed light scans on the exposure target 955. The deflecting means used in this application example is a polygon mirror.

The exposure apparatus 940 comprises a pulsed light generation device PD described above (e.g., the pulsed light generation device 800) a shaping optical system 942, a polygon mirror 953, an objective optical system 944, an exposure target support table 945 at which the exposure target 955 is held and a drive mechanism 946 that drives the exposure target support table 945 in a horizontal plane. The shaping optical system 942, constituted with a plurality of lens groups including a collimating lens, shapes ultraviolet pulsed light output from the pulsed light generation device PD and allows the shaped ultraviolet pulsed light to enter, via a mirror 943, the polygon mirror 953. The polygon mirror 953 is a rotary polygon mirror. In the example presented in FIG. 19, a polygon mirror taking an equilateral hexagonal shape in a plan view, is rotatably driven around an axis extending perpendicular to the sheet by a mirror drive mechanism. Via the objective optical system 944, constituted with a plurality of lens groups including an fθ lens and a condenser lens, an image is formed on the exposure target 955 held on the exposure target table 945 with the ultraviolet pulsed light scanning the exposure target 955 by the polygon mirror 953. The exposure target 955 is moved by the exposure target table 945 along a direction perpendicular to the scanning direction along which the exposure target 955 is scanned with the ultraviolet pulsed light from the polygon mirror 953 (i.e., the exposure target 955 is moved along a direction perpendicular to the sheet).

The operations of the pulsed light generation device PD, the polygon mirror 953 and the exposure target table 945 are controlled by a control device (not shown). Data indicating a pattern to be drawn on the exposure target 955 are stored in the control device in advance and the control device controls the operations of the pulsed light generation device PD, the polygon mirror 953 and the exposure target table 945 in correspondence to the pattern data stored therein. Through this process, an image of a preset pattern is formed through exposure on the exposure target 955 held at the exposure target table 945.

As explained above, the pulsed light generation device PD enables high-speed ON/OFF control of ultraviolet pulsed light. This means that the ultraviolet pulsed light itself, which is a particularly critical factor in an exposure apparatus that directly draws a pattern with ultraviolent pulsed light without employing a mask, as in this application example, can be controlled with high accuracy, and highly accurate exposure can be ultimately achieved.

It is to be noted that while the polygon mirror 953 is used as the deflecting means in this application example, a deflecting means adopting another structure may be used, instead. For instance, a galvanometer mirror may be used instead of the polygon mirror 953. As a further alternative, two galvanometer mirrors may be combined so as to be set along two directions perpendicular to each other and ultraviolet pulsed light output from the pulsed light generation device PD may be directed to scan the exposure target 955 over the two directions.

Figure 20:
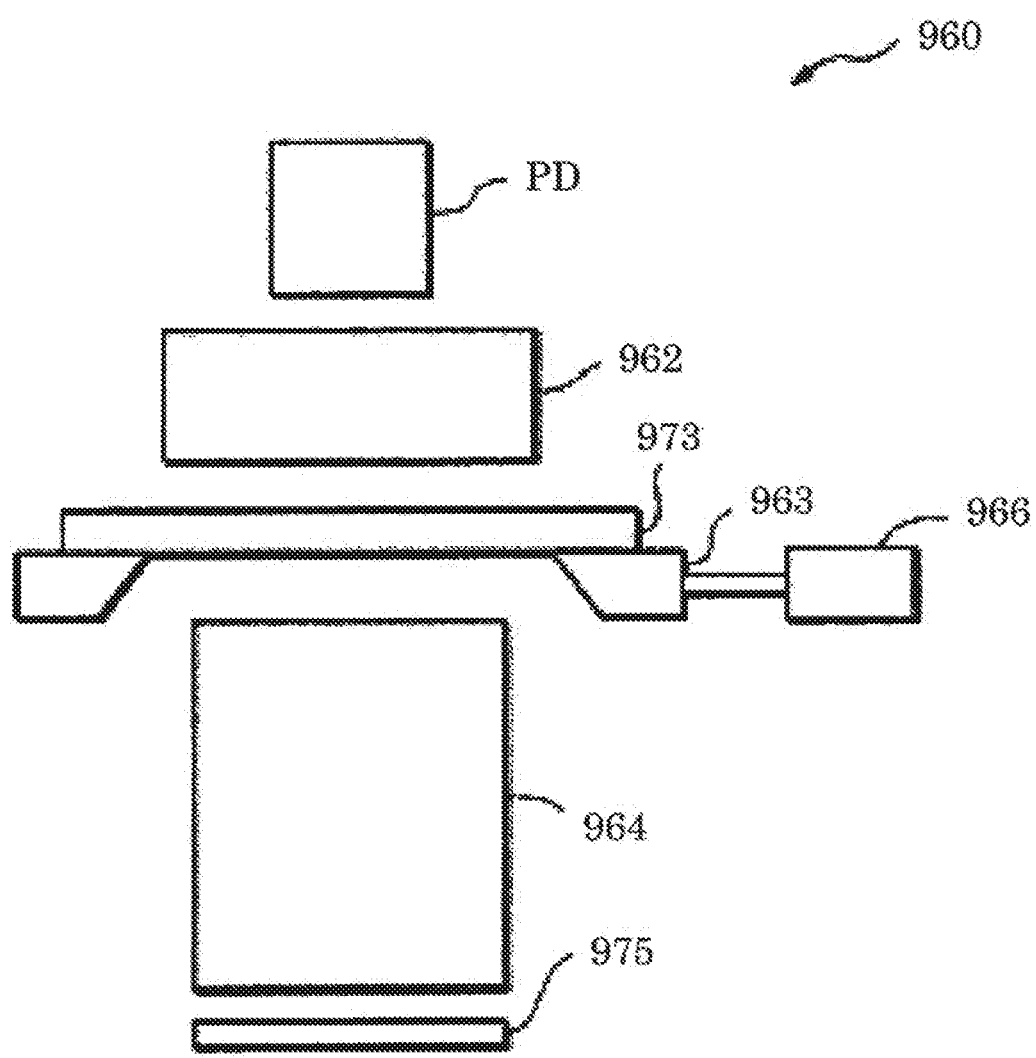
FIG. 20 is a diagram schematically illustrating the configuration of an inspection apparatus, representing a fourth application example of a system having a pulsed light generation device.

An inspection apparatus used in an inspection process through which an inspection target, such as photomask, a liquid crystal panel or a wafer or the like, is inspected, as a fourth application example of a system equipped with the pulsed light generation device PD, will be described next in reference to FIG. 20 schematically illustrating its structure. An inspection apparatus 960 is preferably used to inspect a very fine pattern drawn on an inspection target 973 having optical transparency, such as a photomask.

The inspection apparatus 960 is configured to include the pulsed light generation device PD described above, an illumination optical system 962, an inspection target support stage 963 at which the inspection target 973 is held, a projection optical system 964, a TDI (time delay integration) sensor 975 that detects light from the inspection target 973, and a drive mechanism 966 that moves the inspection target support stage 963 in a horizontal plane. The illumination optical system 962 includes a plurality of lens groups. The illumination optical system 962 adjusts the ultraviolet pulsed light output from the pulsed light generation device PD to have a predetermined light flux, and then irradiates the ultraviolet pulsed light flux onto the inspection target 973 which is held at the inspection target support stage 963. The projection optical system 964 includes a plurality of lens groups and project the light transmitting through the inspection target 973 onto the TDI sensor 975.

In the inspection apparatus 960, the ultraviolet pulsed light output from the pulsed light generation device PD is input to the illumination optical system 962 and adjusted to have a predetermined light flux, and the ultraviolet pulsed light is irradiated onto the inspection target 973 such as a photomask which is held at the inspection target support stage 963. The light from the inspection target 973 (a transmitted light in this application example) has an image of a pattern drawn on the inspection target 973, and the light is projected via the projection optical system 964 onto the TDI sensor 975 to form an image. During this period, a horizontal velocity of the inspection target support stage 963 moved by the drive mechanism 966 and a transfer clock at the TDI sensor 975 are synchronously controlled.

Thus, the image of the pattern on the inspection target 973 is detected by the TDI sensor 975. A comparison between the image of the inspection target 973 detected in this way and a predetermined reference image, which is preset, extracts any defects in the pattern drawn on the inspection target. If the inspection target 973 such as a wafer has no optical transparency, the same configuration can be achieved by guiding a reflected light from the inspection target so that the light is incident upon the projection optical system 964 and then propagates to the TDI sensor 975.

Because the inspection apparatus 960 is configured to include the pulsed light generation device PD capable of providing a ultraviolet pulsed light with high output and high-quality beam and thus, it can be expected to contribute to an improvement in inspection accuracy during the inspection process and to a reduction in the length of time required for the inspection process.

It is to be noted that the present invention is not limited to the particulars of the embodiments described above and any other mode conceivable within the scope of the technical teaching of the present invention is within the scope of the present invention. In addition, any combination of the embodiments described above is also within the scope of the present invention.

What is claimed is:

1. A pulsed light generation device, comprising:
    a first optical fiber through which first pulsed light and second pulsed light, having an intensity that decreases while an intensity of the first pulsed light increases, and increases while the intensity of the first pulsed light decreases, having been multiplexed and entered therein, are propagated; and
    a second optical fiber at which the first pulsed light, having exited the first optical fiber and entered therein, is amplified while being propagated therein, wherein:
    at the first optical fiber, phase modulation occurs in the first pulsed light due to cross phase modulation caused by the second pulsed light; and
    self-phase modulation occurring in the first pulsed light at the second optical fiber is diminished by the phase modulation having occurred at the first optical fiber.

2. The pulsed light generation device according to claim 1, wherein:
    the second pulsed light has a peak intensity higher than the peak intensity of the first pulsed light.

3. The pulsed light generation device according to claim 2, wherein:
    a maximum value of the second pulsed light entering the second optical fiber is lower than a maximum value of the first pulsed light entering the second optical fiber or is zero.

4. The pulsed light generation device according to claim 1, wherein:
    the second pulsed light has a maximum value at time points both before and after a time point at which the intensity of the first pulsed light peaks.

5. The pulsed light generation device according to claim 1, further comprising:
    a separation element disposed between the first optical fiber and the second optical fiber, which separates the first pulsed light and the second pulsed light from each other.

6. The pulsed light generation device according to claim 5, further comprising:
    a first laser light source that emits the first pulsed light; and
    a second laser light source that emits the second pulsed light, wherein:
    wavelength of the first pulsed light and wavelength of the second pulsed light are different from each other; and
    the separation element is a wavelength selection filter.

7. The pulsed light generation device according to claim 5, further comprising:
    a first laser light source that emits the first pulsed light; and
    a second laser light source that emits the second pulsed light, wherein:
    polarization direction of the first pulsed light and polarization direction of the second pulsed light are different from each other; and
    the separation element is a polarization beam splitter.

8. The pulsed light generation device according to claim 1, further comprising:
a first laser light source that emits the first pulsed light; and
a second laser light source that emits the second pulsed light.

9. The pulsed light generation device according to claim 1, further comprising:
a third laser light source that emits third pulsed light;
a demultiplexer element that branches the third pulsed light into pulsed light to be propagated through a first optical path and pulsed light to be propagated through a second optical path;
a first modulation element that is disposed in the first optical path and generates the first pulsed light;
a second modulation element that is disposed in the second optical path and generates the second pulsed light; and
a multiplexer element that multiplexes the first pulsed light propagated through the first optical path and the second pulsed light propagated through the second optical path so that multiplexed first pulsed light and second pulsed light are propagated through a third optical path, wherein:
the first optical fiber and the second optical fiber are disposed in the third optical path; and
a polarization beam splitter is disposed between the first optical fiber and the second optical fiber.

10. The pulsed light generation device according to claim 9, wherein:
a third optical fiber at which the second pulsed light is amplified, is disposed in the second optical path.

11. The pulsed light generation device according to claim 9, wherein:
a partially reflecting element is disposed in the first optical path.

12. The pulsed light generation device according to claim 1, further comprising:
a wavelength conversion unit at which a wavelength of the first pulsed light, having exited the second optical fiber and entered therein, is converted as the first pulsed light is propagated therein.

13. The pulsed light generation device according to claim 12, wherein:
the wavelength conversion unit includes a plurality of nonlinear optical crystals and converts the wavelength of the first pulsed light to a wavelength in an ultraviolet range.

14. An exposure apparatus, comprising:
a pulsed light generation device according to claim 1;
an exposure target support unit at which an exposure target is held;
a pattern forming unit that forms a predetermined pattern light from pulsed light output from the pulsed light generation device; and
a projection optical system via which the pattern light is projected onto the exposure target held at the exposure target support unit.

15. An inspection apparatus, comprising:
a pulsed light generation device according to claim 1;
a inspection target support unit at which a inspection target is held;
an illumination optical system that irradiates pulsed light output from the pulsed light generation device onto the inspection target held at the inspection target support unit; and
a projection optical system that projects light from the inspection target onto a detector.

16. A pulsed light generation method, comprising steps of:
multiplexing first pulsed light and second pulsed light, having an intensity that decreases while an intensity of the first pulsed light increases, and increases while the intensity of the first pulsed light decreases, and causing the multiplexed first pulsed light and second pulsed light to enter a first optical fiber to be propagated therein;
causing the first pulsed light, having exited the first optical fiber, to enter a second optical fiber and amplifying the first pulsed light as the first pulsed light is propagated through the second optical fiber; and
diminishing phase modulation occurring in the first pulsed light at the second optical fiber, attributable to self-phase modulation, with phase modulation occurring in the first pulsed light at the first optical fiber, attributable to cross phase modulation caused by the second pulsed light.

17. The pulsed light generation method according to claim 16, wherein:
the second pulsed light has a peak intensity higher than a peak intensity of the first pulsed light.

18. The pulsed light generation method according to claim 17, wherein:
a maximum value of the second pulsed light entering the second optical fiber is lower than a maximum value of the first pulsed light entering the second optical fiber or is zero.

19. The pulsed light generation method according to claim 16, wherein:
the second pulsed light has a maximum value at time points both before and after a time point at which the intensity of the first pulsed light peaks.

20. A pulsed light generation method according to claim 16, wherein:
the first pulsed light and the second pulsed light are separated from each other by a separation element disposed between the first optical fiber and the second optical fiber.

21. The pulsed light generation method according to claim 20, wherein:
the first pulsed light is generated from a first laser light source;
the second pulsed light is generated from a second laser light source;
wavelength of the first pulsed light and wavelength of the second pulsed light are different from each other; and
the separation element is a wavelength selection filter.

22. The pulsed light generation method according to claim 20, wherein:
the first pulsed light is generated from a first laser light source;
the second pulsed light is generated from a second laser light source;
polarizing direction of the first pulsed light and polarizing direction of the second pulsed light are different from each other; and
the separation element is a polarization beam splitter.

23. The pulsed light generation method according to claim 16, wherein:
the first pulsed light is generated from a first laser light source; and
the second pulsed light is generated from a second laser light source.

24. The pulsed light generation method according to claim 16, wherein:
  third pulsed light is emitted from a third laser light source;
  the third pulsed light is branched into pulsed light to be propagated through a first optical path and pulsed light to be propagated through a second optical path;
  the first pulsed light is generated in the first optical path;
  the second pulsed light is generated in the second optical path;
  the first pulsed light and the second pulsed light are multiplexed; and
  the first pulsed light and the second pulsed light are separated from each other by a polarization beam splitter disposed between the first optical fiber and the second optical fiber.

25. The pulsed light generation method according to claim 24, wherein:
  the second pulsed light is amplified by a third optical fiber.

26. The pulsed light generation method according to claim 24, wherein:
  the peak intensity of the first pulsed light is lowered by partially reflecting the first pulsed light from the first optical path.

27. The pulsed light generation method according to claim 16, wherein:
  the first pulsed light having exited the second optical fiber enters a wavelength conversion unit and a wavelength of the first pulsed light is converted as the first pulsed light is propagated through the wavelength conversion unit.

28. The pulsed light generation method according to claim 27, wherein:
  the wavelength of the first pulsed light is converted to a wavelength in an ultraviolet range via a plurality of nonlinear optical crystals included in the wavelength conversion unit.

* * * * *